United States Patent
Xu et al.

(10) Patent No.: US 10,564,122 B1
(45) Date of Patent: Feb. 18, 2020

(54) ELECTROPHORETIC SOIL NUTRIENT SENSOR FOR AGRICULTURE

(71) Applicant: Iowa State University Research Foundation, Inc., Ames, IA (US)

(72) Inventors: Zhen Xu, Ames, IA (US); Liang Dong, Ames, IA (US); Ratnesh Kumar, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 77 days.

(21) Appl. No.: 15/789,033

(22) Filed: Oct. 20, 2017

Related U.S. Application Data

(60) Provisional application No. 62/411,315, filed on Oct. 21, 2016.

(51) Int. Cl.
| | |
|---|---|
| *G01N 27/447* | (2006.01) |
| *G01N 27/453* | (2006.01) |
| *G01N 33/24* | (2006.01) |
| *A01C 21/00* | (2006.01) |
| *G01N 30/64* | (2006.01) |

(52) U.S. Cl.
CPC ..... *G01N 27/44791* (2013.01); *A01C 21/007* (2013.01); *G01N 27/44704* (2013.01); *G01N 33/24* (2013.01); *G01N 2030/645* (2013.01); *G01N 2033/245* (2013.01)

(58) Field of Classification Search
CPC ........ G01N 27/44791; G01N 2033/245; A01C 21/002; A01C 21/007
See application file for complete search history.

(56) References Cited

U.S. PATENT DOCUMENTS

| | | | |
|---|---|---|---|
| 5,355,815 A | | 10/1994 | Monson |
| 5,545,303 A | * | 8/1996 | Schasfoort ......... G01N 27/4473 |
| | | | 204/451 |

(Continued)

FOREIGN PATENT DOCUMENTS

WO     WO 97/42494 A1 * 11/1997 ............. G01N 27/26

OTHER PUBLICATIONS

Kumar et al., "Determination of hydrazines by chip electrophoresis with contactless conductivity detection," Electrophoresis 2011, 32, 920-925 (Year: 2011).*

(Continued)

*Primary Examiner* — Alexander S Noguerola
(74) *Attorney, Agent, or Firm* — McKee, Voorhees & Sease, PLC

(57) ABSTRACT

An electrophoresis chip-based setup for detection of different ions in buffer solution. The device is able to differentiate ions in, e.g., real soil or other solutions, and to detect concentration of a specific ion in the solution. Fabrication of the electrophoresis chip can use a soft lithography based molding process. The chip can be made out of PDMS on a glass substrate where on-chip valves were used to control timing of injecting sample and buffer solutions. Detection electrodes are used to detect the presence of ions over a period of several minutes. A controllable high voltage power supply system and related signal acquisition, processing and detection setup can be implemented with the sensor in a system. A microfluidic system for automated collection of soil sample through a porous ceramic and using vacuum suction can be used.

20 Claims, 10 Drawing Sheets
(8 of 10 Drawing Sheet(s) Filed in Color)

(56) References Cited

U.S. PATENT DOCUMENTS

| | | | | |
|---|---|---|---|---|
| 5,798,940 | A | * | 8/1998 | Bratton .................. G01V 9/007 204/406 |
| 5,887,491 | A | * | 3/1999 | Monson .................. G01N 1/16 73/864.74 |
| 6,280,589 | B1 | * | 8/2001 | Manz ....................... C07K 1/26 204/451 |
| 6,627,446 | B1 | * | 9/2003 | Roach .............. G01N 27/44704 204/451 |
| 6,926,864 | B2 | * | 8/2005 | Peeters ................. B01L 3/5025 422/50 |
| 7,111,501 | B2 | * | 9/2006 | Rocklin ................. G01N 30/34 73/53.01 |
| 7,216,555 | B2 | | 5/2007 | Drummond et al. |
| 7,575,069 | B2 | | 8/2009 | Pavlik |
| 8,381,582 | B2 | * | 2/2013 | Dahan .................. G01N 33/246 73/152.25 |

OTHER PUBLICATIONS

ChipGenie® edition E product description, downloaded Mar. 25, 2019 from https://www.microfluidic-chipshop.com/catalogue/instruments/editione/ (Year: 2019).*

Laugere et al., "On-Chip Contactless Four-Electrode Conductivity Detection for Capillary Electrophoresis Devices," Anal. Chem. 2003, 75, 306-312 (Year: 2003).*

Bound, Geoffrey P., "Determination of Nitrate in Soil Pastes by Ion Selective Electrodes", J. Sci. Fd Agric. 1977, 28, pp. 501-505. Manuscript received Oct. 16, 1976.

Drossman, Howard et al., "High-Speed Separations of DNA Sequencing Reactions by Capillary Electrophoresis", Anal. Chem. 1990, 62, pp. 900-903.

Lin, Che-Hsin et al., "Double-L Injection Technique for High Performance Capillary Electrophoresis Detection in Microfluidic Chips", Journal of Micromechanics and Microengineering, 14 (2004), pp. 639-646.

Wang, Qinggang et al., "Mobility-based Selective On-line Preconcentration of Proteins in Capillary Electrophoresis by Controlling Electroosmotic Flow", Journal of Chromatography A, 1025 (2004), pp. 139-146.

Tanyanyiwa, Jatisai et al., "High-Voltage Capacitively Coupled Contactless Conductivity Detection for Microchip Capillary Electrophoresis", Analytical Chemistry, vol. 74, No. 24, pp. 6378-6382. Dec. 15, 2002.

Zemann, Andreas J., "Capacitively Coupled Contactless Conductivity Detection in Capillary Electrophoresis", Electrophoresis 2003, 24, pp. 2125-2137.

360 Yield Center, pp. 1-14, 360 SoilScan Setup Instructions, published 2016.

* cited by examiner

ELECTROPHORETIC SOIL NUTRIENT SENSOR FOR AGRICULTURE

CROSS-REFERENCE TO RELATED APPLICATIONS

This application claims the benefit of Provisional Application U.S. Ser. No. 62/411,315 filed on Oct. 21, 2016, all of which is herein incorporated by reference in its entirety.

GOVERNMENT RIGHTS CLAUSE

This invention was made with Government support under Grant Number CCF1331390 and IIP-1602089 awarded by the National Science Foundation. The government has certain rights in the invention.

I. BACKGROUND OF THE INVENTION

A. Field of the Invention

The present invention relates to electrochemical sensing and, in particular, to real-time, in situ sensing. One example is sensing ionic species in soil on-the-go.

Among the existing methods of nutrient sensing, ion-selective electrodes are among the most promising, yet even those are limited in scope due to use of ion-selective membranes which have limited life, and hence not suited for prolonged in-situ applications. In contrast, we present an electrophoresis based label-free inorganic ions sensor for detecting soil nutrient components. This method is based on the facts that ions have different migration rates under an applied electrical potential because of their mobility difference in buffer solution. We developed an electrophoresis chip-based setup for detection of different ions in buffer solution. The device is demonstrated to differentiate anions (e.g., nitrate, perchlorate, sulphate, dihydrogen phosphate, and hydrogen phosphate in a solution extracted from soil) and to detect concentration of a specific ion in the solution. The electrophoresis chip has been manufactured using soft lithography based molding process. The chip was made out of PDMS on a glass substrate where on-chip valves has been placed to control timing of injecting buffer and sample solutions. The detection electrodes have been used to detect the presence of ions over a period of several minutes. A complete sensing system integrates the sensing mechanism described above with microfluidics for sample intake and filtration, excitation source for generation of electrical potential, and readout mechanism. The approach leads to a practical and dependable sensing mechanism for in-situ soil nutrient sensing. The system includes a gas-controlled micro-valve to control on/off status of sample/buffer injection channels to overcome sample leakage problem for higher performance.

All industries that have stake in agriculture and with interest in Internet-of-Things can implement the invention. One limiting example is sustainable agriculture applications, but it is applicable to other domains where sample solution may be extracted, such as water quality, food safety, and bodily fluids.

B. Problems in the Art

The field of sensing for chemicals is burgeoning. Advancements in computational power per unit dollar and miniaturization have allowed a wide variety of approaches to attempt to improve chemical sensing.

Heretofore, it was typical to bring analyte samples to laboratory setups for a variety of chemical sensing and differentiation tasks. Demands for on-site, in situ, real-time sensing exist such for site-specific nutrient management in agriculture, where 30-40% of applied nutrients are wasted due to lack of knowledge of site-specific plant needs, and those excess nutrients act as pollutants to waterways and atmosphere. However, on-site sensing presents a number of challenges.

For example, analyte collection and handling outside lab settings can be antagonistic with durability, precision, and accuracy. By further example, some chemical measurement techniques require expensive, complex, and/or sensitive equipment that can be antagonistic with on-the-go, out-of-doors, non-laboratory sample collection and measurement. Still further, demands for small form factor can be antagonistic with on-the-go, out-of-doors analyte collection and presentation, as well as chemical constituent measurement.

One example of such issues is with real-time, in situ, agricultural soil sensing. In the case of maize, nitrogen is essential for crop development. Yet farmers have an ongoing dilemma between the crop's need for nitrogen versus cost of resources needed for, and environmental concerns with, applying nitrogen. Put simply, it would be ideal if nitrogen could be applied liberally across a field without concern for whether it is needed or not, or how much is needed. However, this is tremendously cost-ineffective and wasteful. It can result in run off into the streams and water supplies, and production of greenhouse gases as nitrous-oxide. Furthermore, on a macro level, the resources needed to manufacture the quantities of nitrogen fertilizer to meet demand must be taken into account.

Therefore, it could be extremely beneficial to sense nitrogen levels in soil in situ and in real-time, or close to real time. This could allow mapping of sensed nitrogen levels across a field and use of that map for modulation of amount of subsequent nitrogen application. For example, certain parts of a field may be higher in nitrogen content than others. The amount of nitrogen application could be reduced for those parts. On a macro-level, this could reduce the demand and manufacturing resources for such fertilizer, as well as reduce the amount placed in-ground.

At least some of these issues also exist for other soil nutrients and fertilizers to compensate for deficiencies. Still further, analogous issues can exist for other sensing applications in other contexts. Non-limiting examples include water quality, food safety, and bodily fluid applications. Therefore, there is room for improvement in this area of technology.

Several methods have been developed to measure ions, such as using ion-selective electrodes (ISEs) and ion-sensitive field-effect transistors (ISFETs) (Bound 2006, Price et al. 2003). Optical techniques are also applied for ion sensing, such as Raman Spectroscopy (B. Zhang et al. 2008) and Reflectance Spectroscopy (Yew et al. 2014). Our application of electrophoresis in ion detection is unique, while other applications and improvements have been reported. For example, capillary electrophoresis has been extensively used for separation of DNA in genetic engineering (W Hendrickson el, 1984; H Drossman et al. 1990), monitor chemical reactions (A T Woolley et al. 1998), and analyze larger molecules in clinical applications. Capacitively coupled contactless conductivity detection ($C^4D$) has become a widely accepted detection method in capillary electrophoresis for analytes (Andreas J. Zemann 2003). A number of chip-based electrophoresis devices have been developed based on C4D technology (J. Tanyanyiwa el 2002; Q. Wang et al. 2004). To overcome sample leakage behavior, double-L injection technique was developed for high performance (Che-Hsin Lin et al. 2004). A voltage-driven controlled electric field traveling system is applied in electrophoresis microchips to reduce excitation voltage for separation (Lung-Ming Fu et al. 2003). To the best of our knowledge, there is no proof-of-concept for electrophoresis based ion separation and detection.

II. SUMMARY OF THE INVENTION

A. Objects

It is therefore principal object, feature, aspect, or advantage of the present invention to provide apparatus, systems, and methods which solve problems or address deficiencies in the state-of-the-art.

Other objects, features, aspects, advantages of the invention include an apparatus, system, or method as above described which:

a. can balance a number of competing and sometimes antagonistic factors;
b. can measure in situ, including robustness and durability for outdoors and in soil uses, and for a long useful operational life without having to change out materials;
c. can include automatic sample collection and preparation, including with minute sample sizes;
d. can provide real time or substantially real time read out to users and operators;
e. can be miniaturized and even micronized to small form factor;
f. is relatively economical with respect to materials and operation;
g. can produce sufficiently accurate and precise measurements, including specificity and sensitivity to analytes of interest;
h. can be applied in a variety of the contexts;
i. can be utilized to inform a subsequent action, such as controlling an actuator to compensate for the estimated levels of chemicals in the analyte;
j. can be integrated with wireless interface for remote access of data and remote control of sensor; wireless interface allows means no wires running to the sensor for data-collection, interaction and/or powering, and makes it not interfere with farming.

B. Aspects

One aspect of the invention comprises a method for measuring constituent chemicals in an analyte sample in at least substantially real time and in situ. An analyte sample is collected and processed for injection to a microfluidic chip. The analyte sample is combined with a proper buffer solution. The sample/buffer solution is then exposed to a controlled electric field. Ionic species in the combined sample/buffer solution are electrophoretically separated along a microfluidic separation channel. Conductivity of the separated ions is recorded. The conductivity peak occurrence times are compared to reference values correlated to various ionic species of interest. An estimate of presence and concentration of one or multiple ionic species can be made by comparison to the reference values for further action. One example of further action is simply to provide a read-out of the identified ionic species to the operator. Another example of further action would be to use the identified species and/or concentrations thereof by another system. For example, a specific, non-limiting example in agriculture of another system is a fertilizer applicator. The ionic species identification and quantification at different measurement locations across a field can be used to modulate application rate by a fertilizer applicator.

In another aspect of the invention, a sensor comprises a body or chip comprising a microfluidic network. An injection configuration is used to receive an analyte sample and load a buffer solution at one end of an elongated electrophoresis separation channel in the body. A circuit is operatively connected to the body to set up a controllable electric field along the separation channel sufficient to move the analyte along the channel, as well as influence electrophoretic separation of ionic species over time. A detector circuit positioned at the far end of the separation channel measures conductivity where the analyte mixed with buffer solution flows past to an outlet. The detector generates an output signal of conductivity measurements to correlate to one or more ionic species and their concentrations.

Another aspect of the invention comprises a system that utilizes a sensor such as described above. An analyte collector is operatively connected to the sensor to automatically sample an analyte material and present the sample at an injection point of microfluidic circuit of the sensor. A controller controls an electrophoretic separation electric field along the separation channel of the microfluidic circuit. An electric field is also used for loading of the sample and buffer. Conductivity measurements after electrophoretic separation are taken with a conductivity detector. The output signal is sent to a processor which can compare conductivity measurements to reference calibrations. The processor can be connected to other components to control some further action in response to the estimated presence and concentration of one or more ionic species of interest. In one example, further action comprises using the sensed measurements as input to a precision agriculture system that controls steering of an agricultural tractor and also issues instructions to any towed implement for precision site-specific application. One example is that the system could sample soil for presence of soil nutrients of interest in a crop field. The measurements can be obtained on-the-go, in real time, and in situ, and be used to generate a field map that is populated with measured nutrient values from the sensor correlated to the geospatial measurement locations in the field. That map could be used either immediately or at a later time to allow the precision ag system to modulate application of fertilizer in accordance to the field map.

III. BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates the following regarding one exemplary embodiment according to the invention: (a) a schematic of the microfluidic electrophoretic ion sensor system; (b) a photograph of the developed microfluidic electrophoretic ion sensor system consisting of an electrophoresis microchip, a customized printed circuit board (PCB) integrating the two programmable precision high voltage power supply units, a conductivity detection unit, and an Arduino microcontroller; (c) a photograph of the fabricated electrophoresis microchip; (d) a schematic of an electrophoresis microchip, in_electrode is connected to the sinusoidal input and out_electrode is connected to the conductivity detection circuit; (e) a schematic of the operation steps of sampling injection, ion separation, and conductivity detection.

Figure 5:
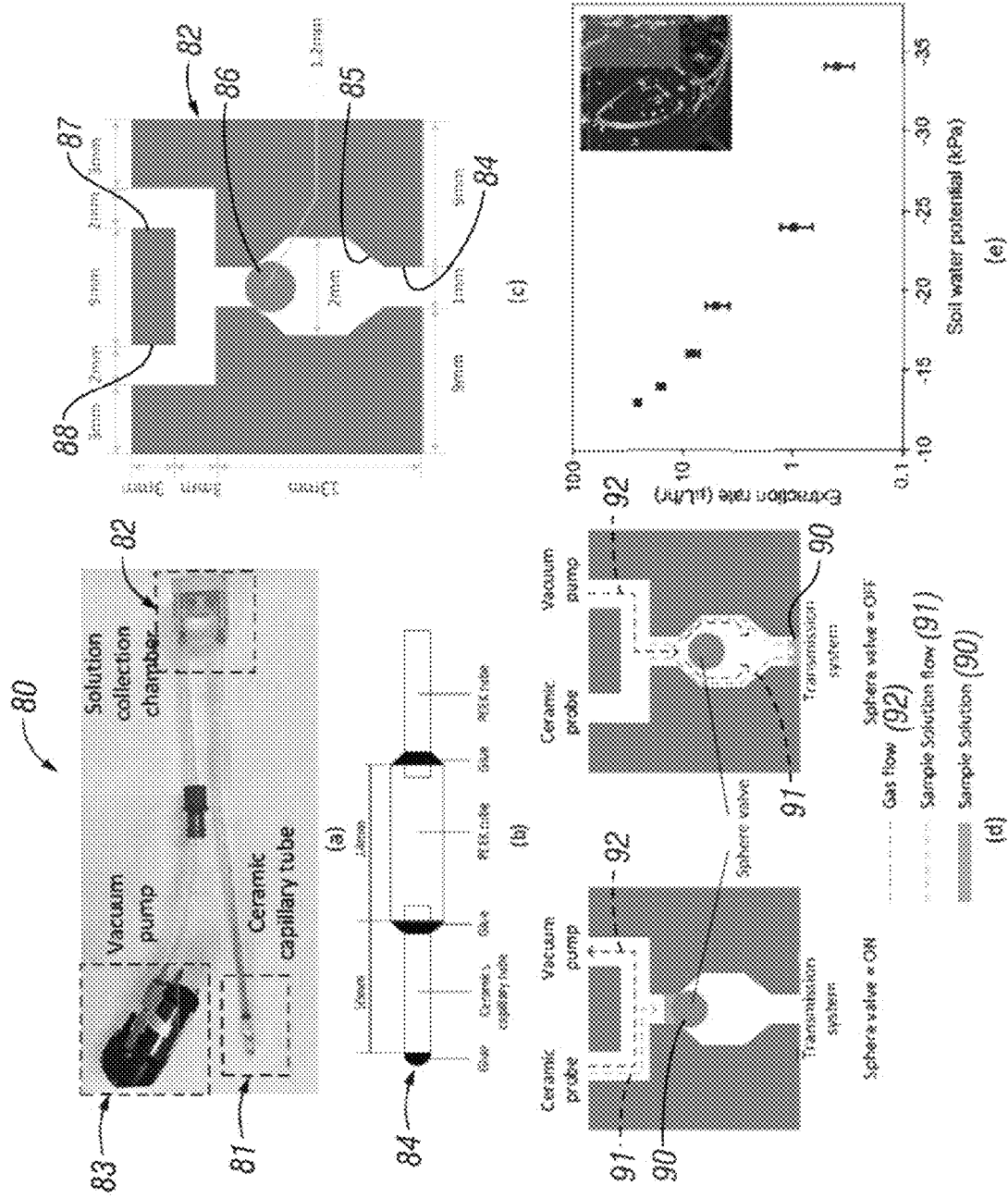

FIG. 5 illustrates examples of the following according to aspects of the invention: (a) a schematic of the soil water extraction unit, consisting of a suction head, a PMMA chamber, and a vacuum pump; (b) a schematic of the suction head, ceramics capillary tube's outer diameter (OD) is 2.3 mm; (c) a schematic of solution collection chamber; (d) ON and OFF working phases of the PMMA soil water collection chamber; (e) measured extraction rates under different soil water potentials.

Figure 6:
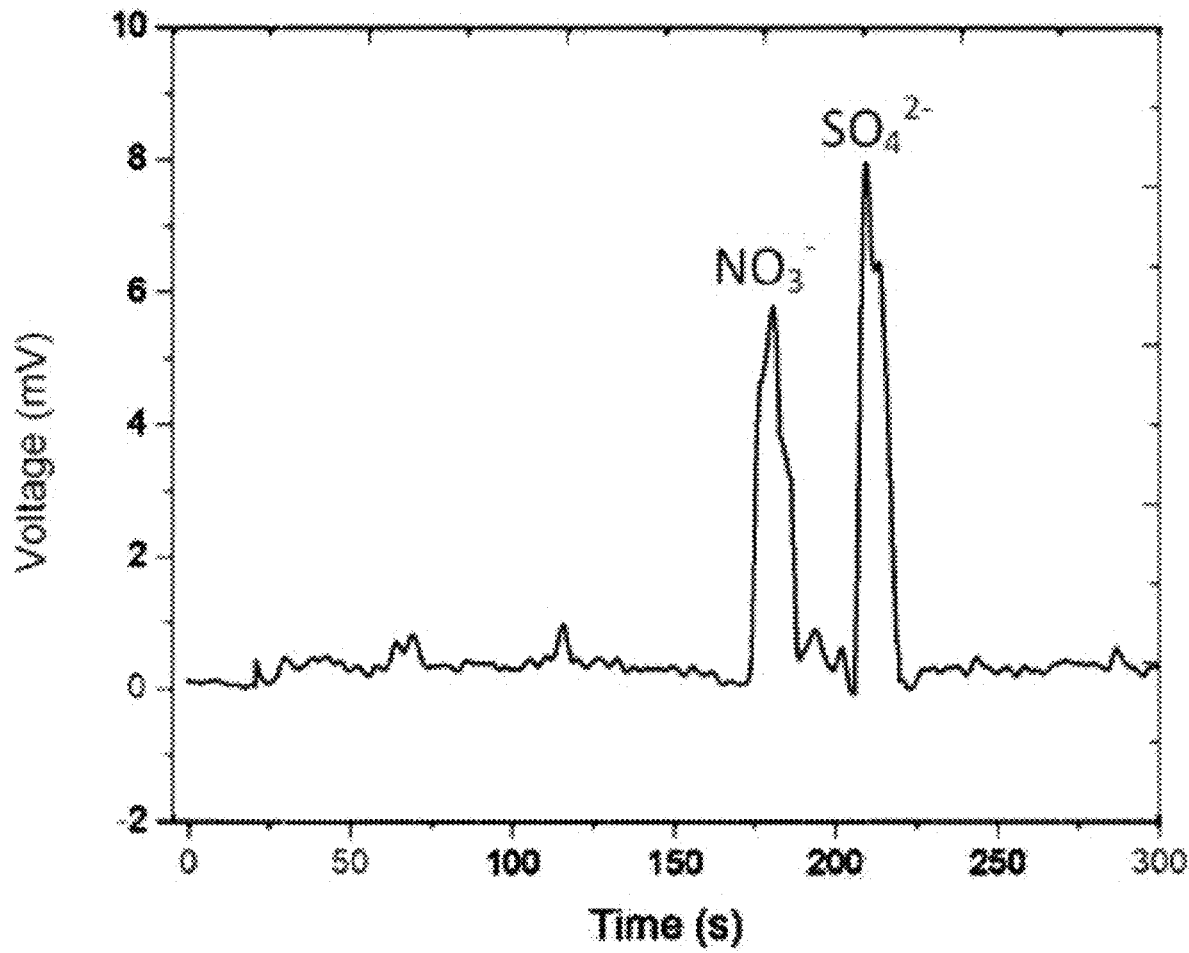

FIG. 6 Illustrates experimental results for separation of $NO_3^-$ from $SO_4^{2-}$ ions in the synthetic sample solution containing only these two ion species according to aspects of the invention.

Figure 7:
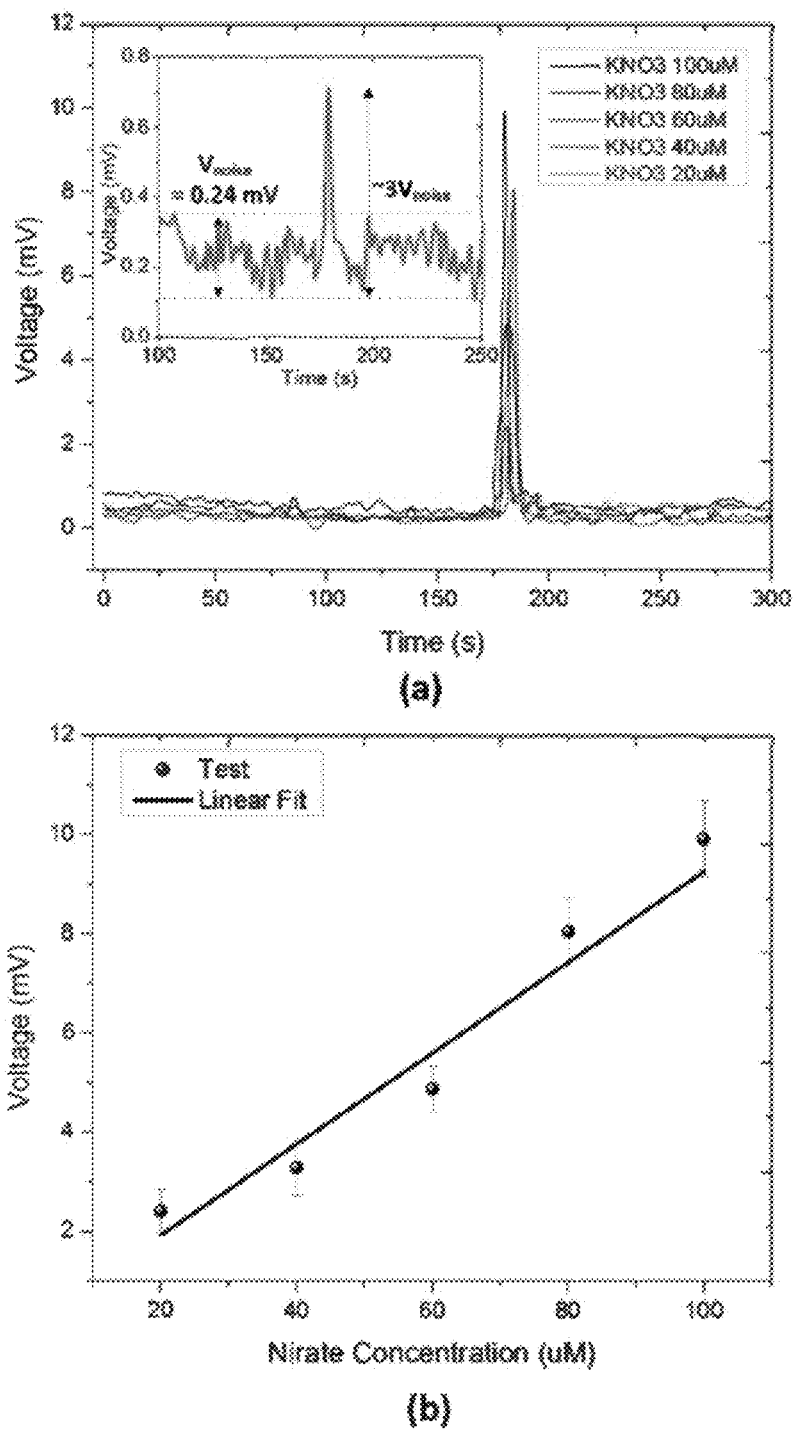

FIG. 7 Illustrates the following aspects of the invention: (a) experimental voltage response of the electrophoresis chip over a period of 300 s to different nitrate ion concentrations; (b) output voltage of the sensor as a function of nitrate ion concentration.

Figure 8:
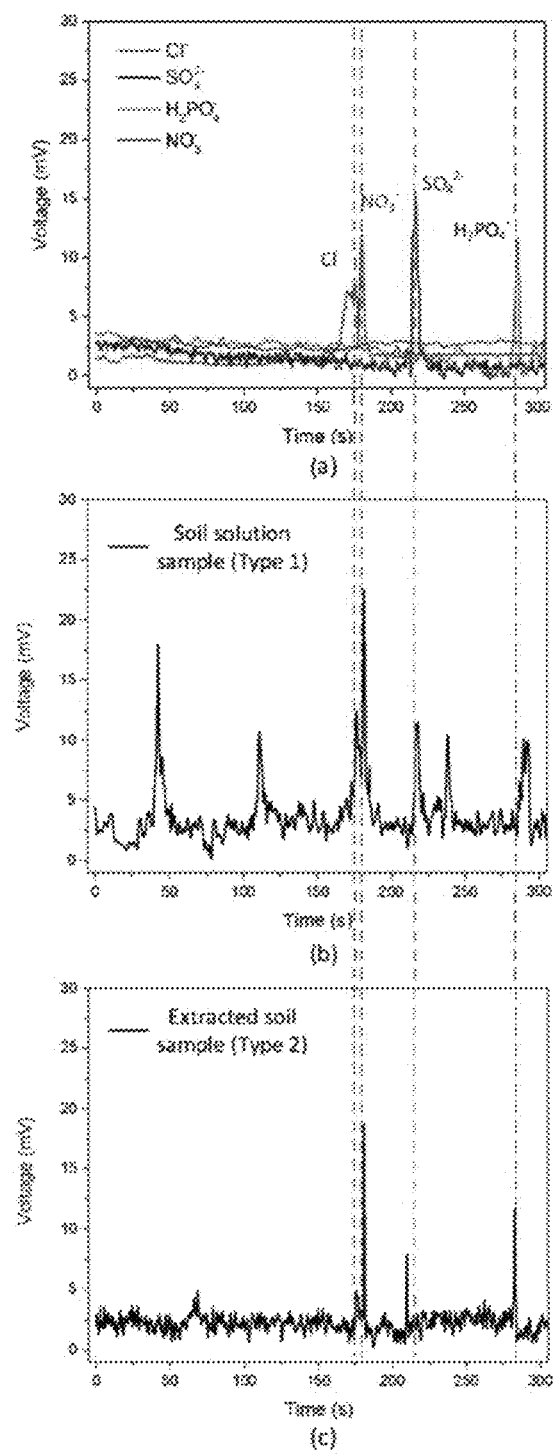

FIG. 8 illustrates electrophoretograms of a device according to the invention showing the separation and detection of anions in different samples: (a) four synthetic samples with each containing only a single anion species ($Cl^-$, $NO^-$, $SO4^{2-}$, or $HPO^-$); (b) real soil solution sample of the first type prepared using the standard shaking and filtering method; and (c) a real sample solution of the second type directly extracted from the soil using the extraction unit. It has less peaks because the smaller pore filter removes many of the particulate matters and microbes.

Figure 9:
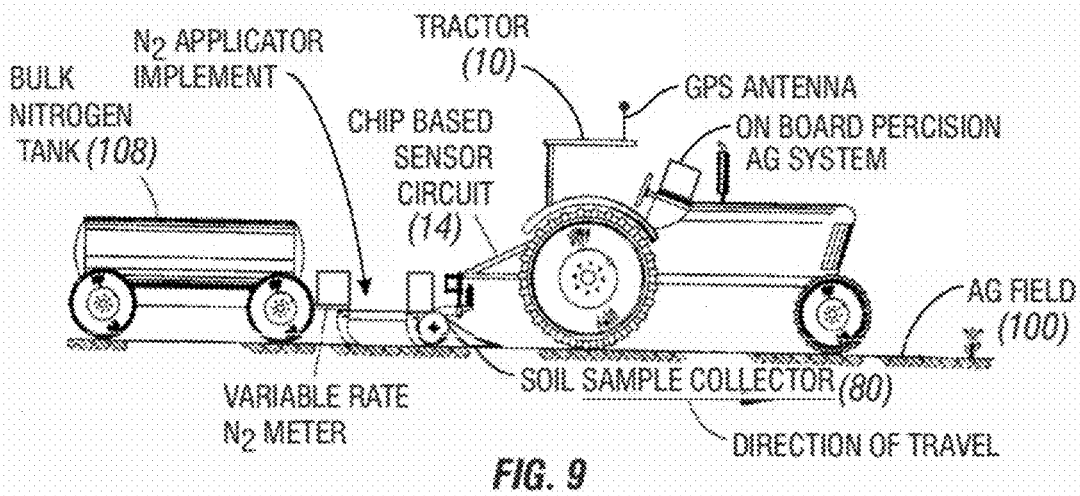

FIG. 9 is a simplified diagram of a tractor and a fertilizer applicator implement for applying fertilizer in an agricultural field. The implement carries one example of implementation of the invention, namely a mechanism to automatically collect soil samples and present them to an on-board soil sensor. The soil sensor can evaluate the soil sample for one or more nutrients and report the results to a controller (such as might be used with a precision ag on-board system). The controller can then modulate fertilizer application rate from the implement according to nutrient levels sensed from the soil.

Figure 10:
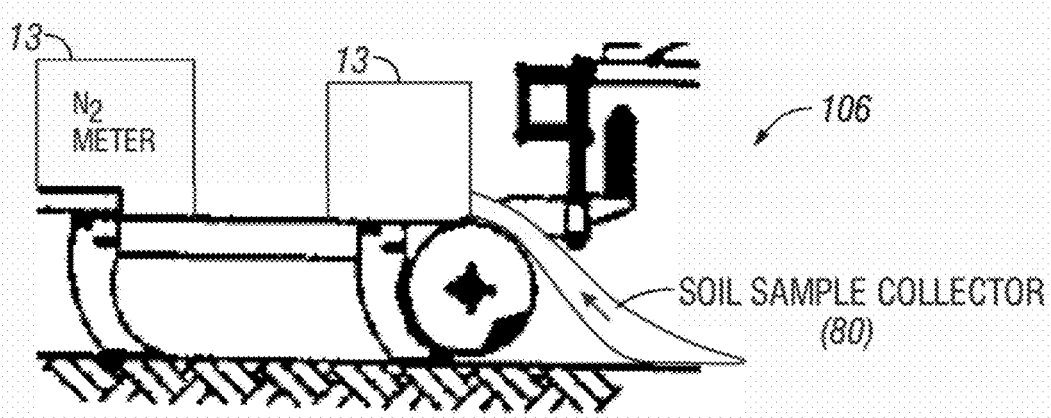

FIG. 10 is an enlarged diagrammatic view of the field working implement of FIG. 9 including a soil collector for gathering and directing soil samples to the on-board soil sensor according to the invention. The soil sensor has an electrophoretic microfluidic circuit and electrical connectivity detector. The soil sensor can inform a nitrogen rate controller how much nitrogen to apply to across the field by correlating detected concentration of nitrates to sampled locations across the field.

Figure 11:
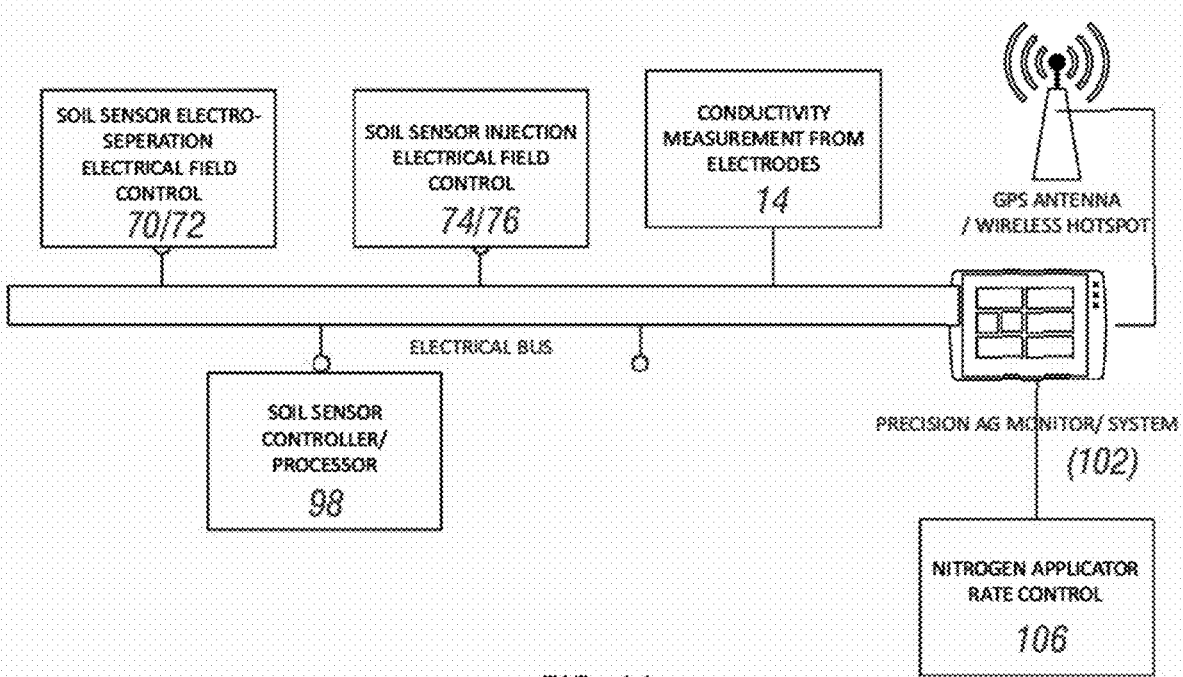

FIG. 11 is a schematic diagram of the system of FIGS. 9 and 10, including communication between the precision ag system on the tractor and the soil sensor. They can communicate with a rate control of a nitrogen applicator. The soil sensor system includes a controllable electrical power supply to generate an injection electric field control and an electroseparation electrical field control. A conductivity measurement from electrodes can be communicated to a controller or processor for further use.

Figure 12:
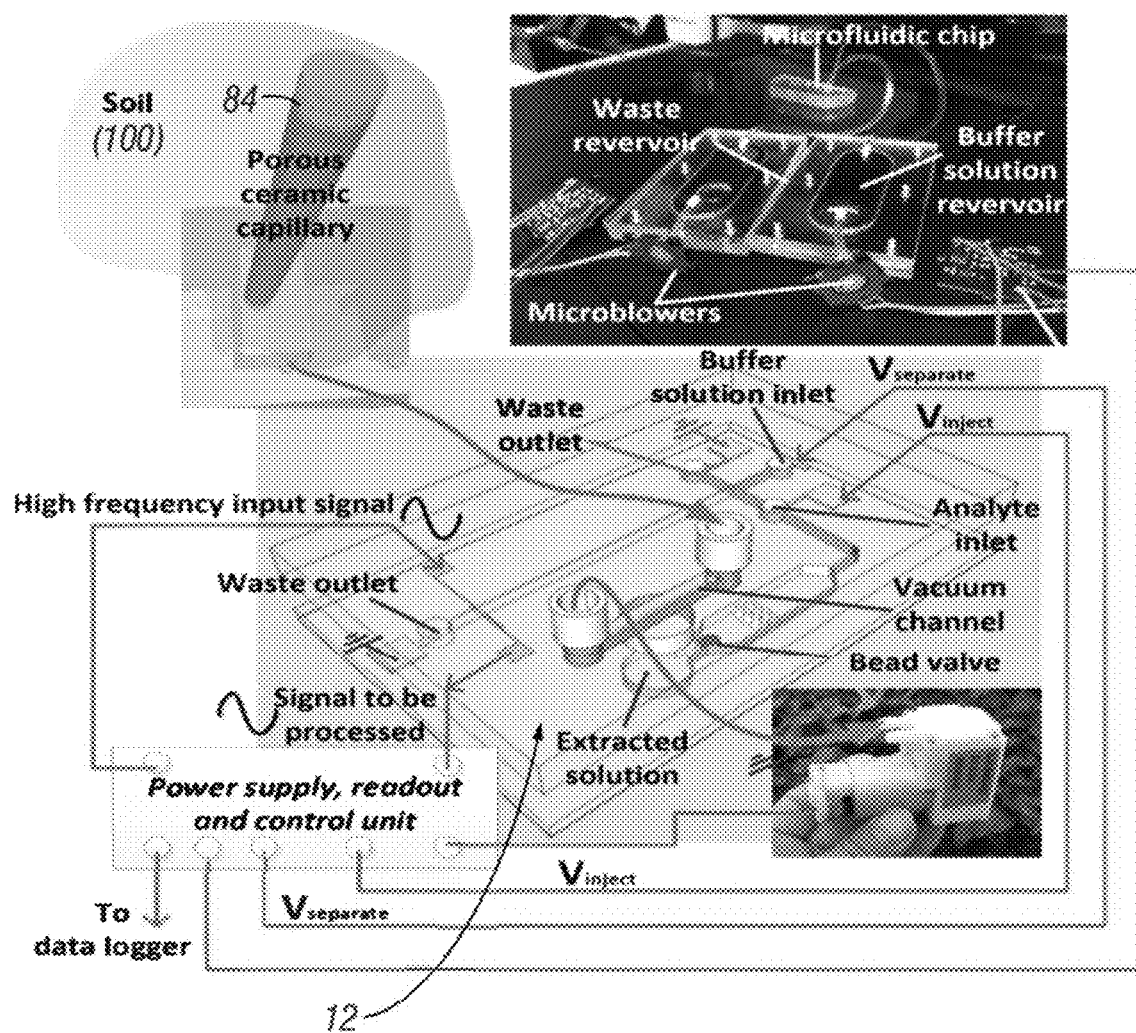

FIG. 12 is a set of diagrammatic views and photos showing prototypes and operating principles of the invention.

IV. DETAILED DESCRIPTION OF EXEMPLARY EMBODIMENTS OF THE INVENTION

A. Overview

For a better understanding of the invention, specific detailed examples of how to make and use the invention will now follow. It is to be understood these are neither exclusive nor inclusive of all forms of embodiments the invention can take.

The examples will mainly focus on use of a sensor for sensing ionic species in soil. However, it is to be understand that uses in other applications by analogous methods, apparatus, and systems are possible. The examples herein are not intended to limit the scope of the invention.

Frequent reference will be taken to the drawings which are incorporated by reference herein. Reference will also be taken to the indicated incorporated by reference References for supplemental information.

B. Generalized Idea

In generalized form, the invention can be embodied in a sensor assembly that has the following features:
   a. a body (e.g. chip) with a microfluidic circuit;
   b. the microfluidic circuit including
      i. an injection section for an analyte sample and a buffer solution;
      ii. an electrophoretic separation channel in operative connection to an electric separation field;
      iii. an output for the sample/buffer solution;
   c. conductivity sensing electrodes operatively positioned at the separation field along the separation channel.

By control of injection of an analyte sample with buffer solution and control of an electric field along the separation channel, electrophoretic separation of one or more ionic species in the sample/buffer can be achieved. By calibration of conductivity measurements and the time-location of their peaks resulting from the separated ions as those go by the detector, ionic species of interest and their concentrations can be identified. Thus, in basically real-time, with the potential of doing so in situ with a source of the analyte (e.g. by collecting samples of an analyte on-the-go), the sensor can output a signal which can be evaluated accordingly. Knowledge of the presence of one or more ionic species of interest in the sample can be utilized for further action.

In one example, this general method can be applied to sensing soil nutrients for agricultural purposes. By appropriate soil sampling on-the-go, collecting quite minute quantities of samples from various locations in a farm field, and the above mentioned electrophoretic analysis, identification of ionic species such as nitrates, phosphates, sulphates, chlorides, potassium, sodium, calcium, can be achieved. A geospatial map of the field relative to sensed nitrate levels can be produced. That map can then be used to inform the farmer as to the amount of nitrogen and other fertilizer to be applied across the field.

As mentioned, the invention is not limited to soil nutrient sensing or agricultural uses. Other potential uses, also non-limiting in nature, such as water quality measurement are mentioned elsewhere herein to give some additional examples.

C. Specific Example

Nutrient Sensing Using Chip Scale Electrophoresis and In Situ Soil Solution Extraction This description reports an electrophoresis based microfluidic ion nutrient sensor for the detection of anions in soil solution samples. The sensor is able to analyze concentration of various anions in extracted soil solutions with high sensitivity as well as high specificity, while it is an approach requiring no labels. The electrophoretic microchip integrates a pair of in-plane conductivity detection microelectrodes. A programmable high voltage power supply unit was designed to achieve precise control over voltage potentials needed for sample and buffer injection and ion separation. An electrical conductivity detector was designed to extract and process the changes in conductivity due to the arrivals of separated anions at the electrodes at various times. An arrival time serves to identify an anionic species, while the peak height indicates the concentration. A soil water extraction device was also designed to extract the soil solution analyte from the bulk soil, by applying vacuum suction. Only a minute amount of solution (on the order of μL) is needed for the electrophoretic measurement. Extracted soil solutions were analyzed for ionic concentrations to demonstrate the feasibility of using this microfluidic sensor, showing a limit of detection of about 7.25 μM.

Introduction

Sensors-enabled nutrient management for sustainable agriculture is of great societal interest [1-4]. In fact, "managing the nitrogen-cycle" is one of the 14 grand challenges put forth by the U.S. National Academy of Engineering. By measuring the available plant nutrients in soil, a more precise nutrient application can be achieved in farming [5, 6]. Sensing the changes in the nutrient ion concentrations is vital for providing the nutrient-sufficient conditions for a maximal plant growth and yield [7]. Therefore, a soil nutrient sensor is important for optimizing nutrient management.

Over the past two decades, many types of soil sensors have been developed to monitor soil properties, including soil moisture [8, 9], pH [10], temperature [11], heavy metal [12], and nutrients [14]. These span various measurement techniques include electrical [8, 14], electromagnetic [15], optical [16], radiometric [17], mechanical [18], acoustic [19], or electrochemical [20]. For the detection of nutrient ions in the soil, common measurement practices include the use of ion chromatography [21], spectrophotometry [22], ion-selective electrodes (ISEs), and electrochemical sensors [23]. Among these, chromatography and spectrophotometry are limited to laboratory settings, while the goal here is design of affordable sensors for site-specific and real-time measurements. ISE-based sensors are field deployable and can convert the activity of a specific ion in a solution into an electrical signal [24]. They, however, rely on specific ion-selective membranes that may degrade over time or may not even be available for certain ions (e.g., for phosphorous ions $PO^{3-}$). Enzymatic electrochemical sensors, using an ion-specific enzyme for molecular recognition, have also been developed to realize detection of a specific ion [25]. Similar to ISEs, this type of sensors is affected by their life time and the availability of the ion-specific enzymes.

To address the issues of sensor life and stability, limited by the recognition agent employed, here we present a label-free design based on the electrophoretic separation of ions and electrical measurements of the conductivity at the end of the electrophoretic channel. There exist other prior applications of electrophoretic separation based sensing. For example, capillary electrophoresis has been used for DNA separation [26], monitoring chemical reactions [27], biomolecules analysis [28], and clinical diagnostics [29]. These applications rely on the fact that bio-particles exhibit different mobility characteristics under an electric potential [30]. The commercial electrophoresis instruments with classic capillaries are often equipped with optical absorption or fluorescence detectors [31-34] and allow for a single-molecule level sensitivity, but are bulky and not meant for field applications [35]. Keeping miniaturization and portability in mind, microfluidic devices for chemical analysis and biological assays have recently received considerable attention [36]. In particular, microchip-scale electrophoresis for separation and detection has been studied for many applications and is considerably compact [37-40]. In contrast to the commercial electrophoresis instruments, the microchip-based electrophoresis devices integrate simple and effective electrical detection methods [41]. This allows downscaling the detector size without scarifying sensitivity. While many microfluidic electrophoretic devices have been reported as cited above, the application to soil nutrient detection remains limited.

This description reports a microfluidic electrophoretic nutrient sensor system capable of separating and quantifying inorganic anions in minute (micro-liter) amounts of soil solution samples. A vacuum suction-based soil solution extraction unit was also designed to enable in situ application. Different ions were separated as they travel along an electrophoretic channel under the influence of an applied electrical field, owing to their differential electrical mobilities. The sensor system 10 includes a microfluidic electrophoresis chip 12 with microelectrodes 40 and 42, a voltage application control unit 13, and an electrical conductivity measurement unit 14, all of which were designed and implemented (FIG. 1(a), (b)). A mixture of anions in the extracted soil water, including chloride (Cl⁻), nitrate (NO₃), sulfate (SO₄), dihydrogen phosphate (H₂PO₄), was successfully separated and detected using the developed system 10, showing ion separation based on travel time along the electrophoretic microchannel 20A, with the detection peak levels corresponding to the ion concentrations. As this device required only a minute amount of the extracted soil solution on the order of microliters, the sensor 10 would make a negligible response to the measured environment. The detected ions contain the most important elements for plant growth, such as Nitrogen (N), Phosphorus (P), and Sulfur (S). Therefore, the developed sensing system 10 has the potential to monitor soil's nutritional health. As mentioned above, no labeling process of analyte-recognition is necessary for the presented sensing approach. In addition, the design of the soil water solution extraction unit (FIG. 5) makes the overall system suitable for an in situ application.

Principle and Design

A. Principle

The electrophoretic separation of the ions in a solution takes place due to the differences in the ion mobilities under the influence of an applied electric field. The two together determine the velocity of an ion in an electrophoretic channel:

$$v = \mu_e E, \quad (1)$$

where v is the ion velocity, $\mu_e$ is the electrophoretic mobility, and E is the applied electric field [42]. The buffer solution used in the electrophoresis microchannel also admits an electroosmotic flow (EOF) under the influence of the same electric field [43]. The EOF is superimposed with the ionic mobility to determine an analyte's overall electrophoretic migration rate, and may reinforce or oppose it [44]. Hence, the net ion-velocity $v_{net}$ is:

$$v_{net} = (\mu_e \pm \mu_{EOF})E, \quad (2)$$

where $\mu_{EOF}$ denotes the EOF mobility. Accordingly, different ionic species arrive at and pass through a detector at different time points while traveling through the electrophoretic microchannel. An electrical conductivity measurement at the microelectrodes, placed at the far end of the microchannel, is a simple means to detect the arrival time and the concentrations of the separated ions. As the ions pass through the detection area, the concentrations of ionic species in the detection area change, thus changing the measured electrical conductivity. These ionic separations and the corresponding changes in the conductivity measurements show up as multiple peaks in a plot of conductivity versus time. At the low concentrations of our setting, the conductivity at any given time is given by [45]:

$$\kappa = \Sigma_i c_i |z_i| \lambda_i \quad (3)$$

where $\kappa$ is the electrolytic conductivity measured at the electrodes, $c_i$ is the molar concentration of the ionic species i in the solution, $z_i$ is the ionic charge, and $\lambda_i$ is the equivalent conductance of the ith ion species.

B. Electrophoretic Microchip

Figure 1:
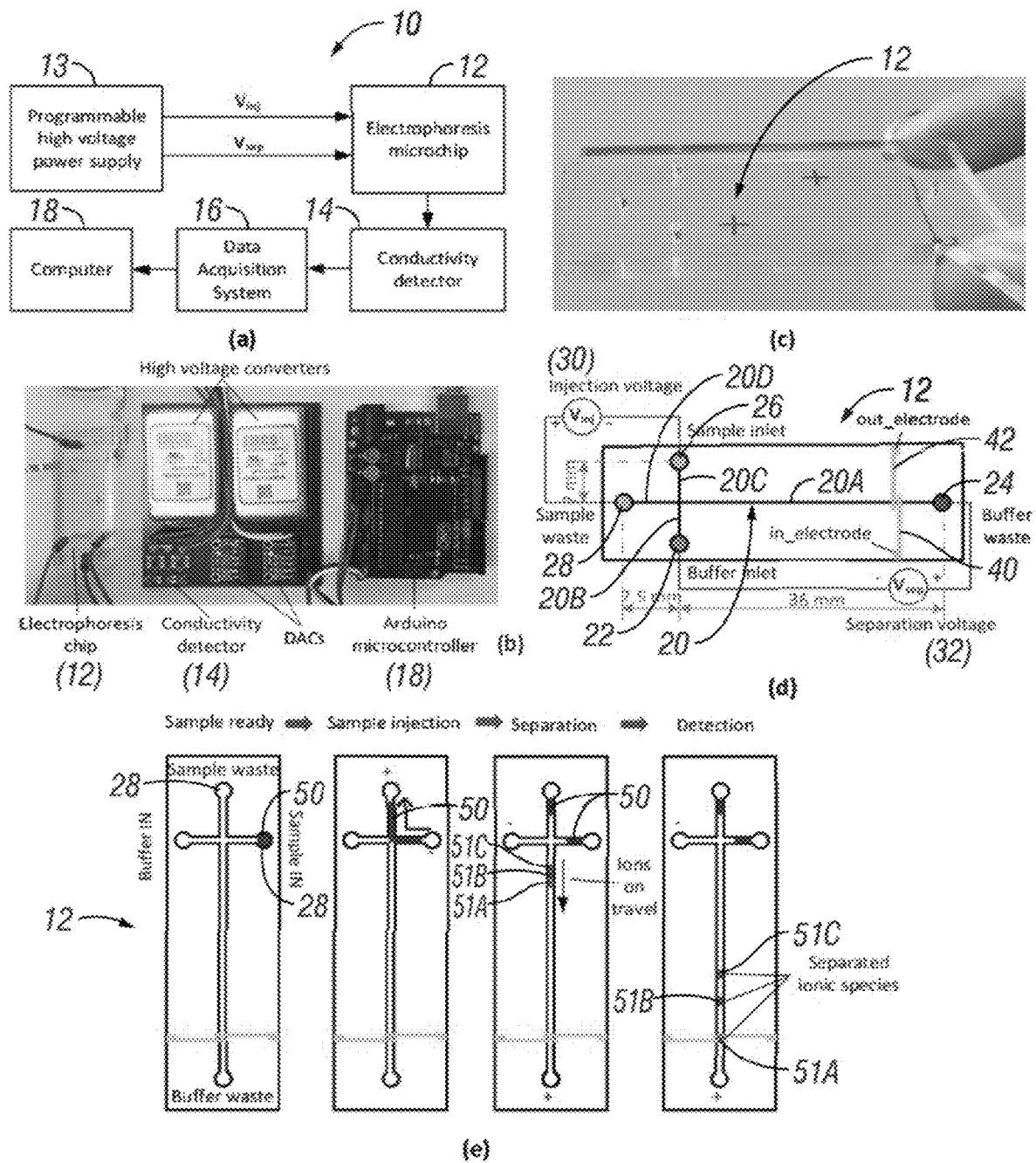

The designed electrophoresis microchip 12 is shown in FIG. 1(c), with its schematic shown in FIG. 1(d). The microchip 12 has the dimensions of 50 mm (length)×25 mm (width)×4 mm (height) and is made of polydimethylsiloxane (PDMS) laid over a thin 130 μm-thick glass slide that is deposited with two gold microelectrodes 40/42 on the face opposite to the PDMS layer. Two perpendicular intersecting microfluidic channels 20B/20C and 20A/20D are located within the PDMS layer. The shorter channel 20B/20C (length: 14 mm) is used for sample loading while the longer one 20A/20D (length: 43.5 mm) for the ion separation. Both the channels are 200 μm wide and 50 μm deep. The two gold microelectrodes 40/42, that are formed on the flip side of the glass substrate, are each 400 μm wide, and orthogonally crossed with the separation channel 20A. The gap between the two microelectrodes is 200 μm [46]. Two sample and buffer inlets 26 and 22, and their corresponding outlets 28 and 24 are located at the ends of the loading 20B/20C and the separation 20A/20D channels, respectively. FIG. 1(e) shows the fluid manipulation processes for the buffer and the analyte 50 solutions, and to separate the ions 51A-C in the analyte solution using electrophoresis.

C. Fabrication Process

Figure 2:
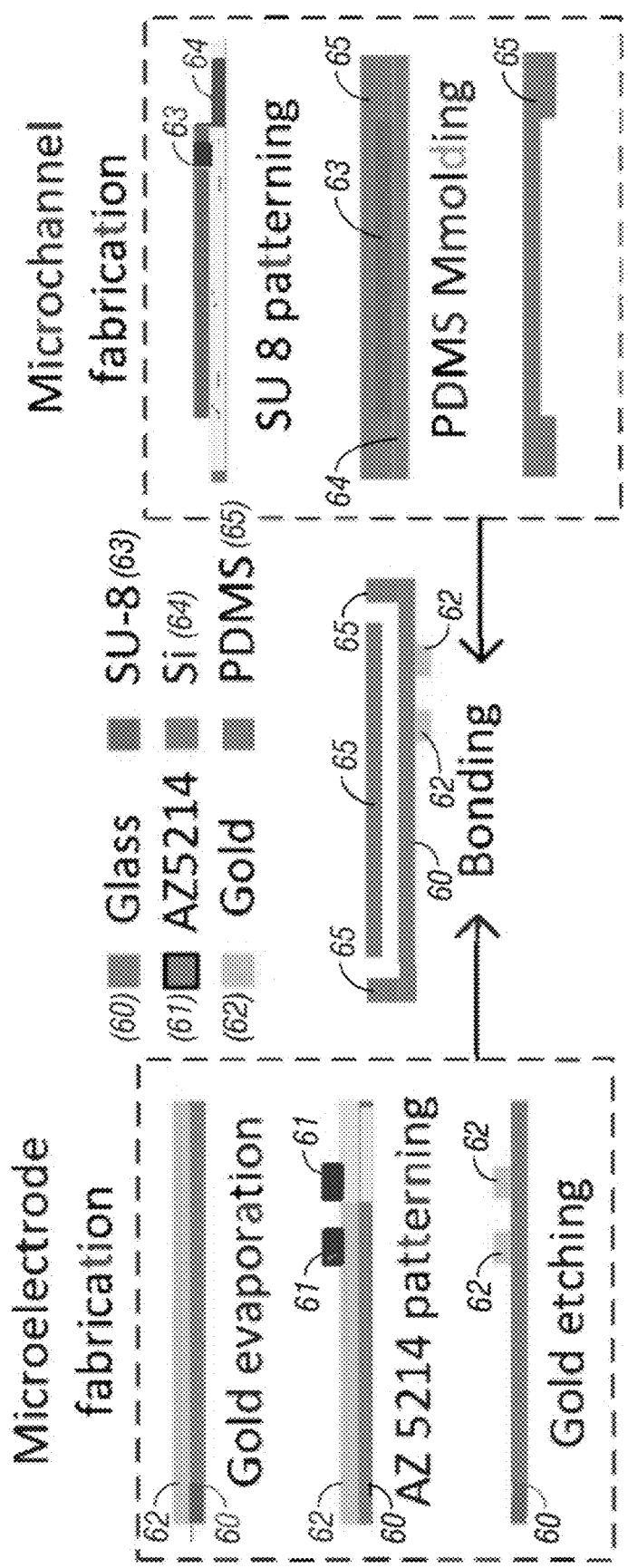
FIG. 2 illustrates a fabrication process for a microfluidic electrophoresis chip according to an aspect of the invention. A side view of the slice along the channel is shown.

The fabrication process for the microchip is schematically shown in FIG. 2. First, the detection electrode materials 62, consisting of 5 nm titanium and 80 nm gold, were sputtered on the surface of the thin glass substrate 60 (60 mm×25 mm×0.13 mm, Superslip® cover glasses, Ted Pella, Redding, Calif.). Subsequently, a 1.5 μm-thick photoresist 61 (AZ 5214, MicroChem Corp, Westborough, Mass.) was spin-coated on the device surface and then photo-patterned by conventional photolithography. After removal of titanium and gold from the unwanted area using an etchant solution (GE-8148, Transene, Danvers, Mass.), the device was flushed with acetone to thoroughly remove the remaining photoresist. Thereby, the microelectrodes 62 were formed.

Next, separately, the PDMS microchannels were fabricated using soft lithography. For this step, a silicon wafer 64 with photoresist SU-8 (ref no. 63) (3050; Microhem, Westborough, Mass.) was spin-coated at 3000 rpm for 30 s to generate 50 μm-thick SU-8 on the surface. Then, the wafer 64 was baked at 65° C. for 5 min and 90° C. for 1 hr. Subsequently, the wafer 64 was exposed to an ultraviolet light with another photomask, baked at 90° C. for 30 min, and developed to form a master mold 65 for the microfluidic channels. Following that, PDMS solution and its curing agent (Sylgard 184, Dow Corning, Auburn, Mich.) with a weight ratio of 10:1 was mixed, degassed, poured on the master mold and thermally cured at 70° C. for 2 hr on a hotplate. The PDMS channel layer 65 was peeled off and necessary holes (see FIG. 2 middle diagram) were formed using a manual punch. Finally, the thin glass substrate 60 was bonded with the PDMS channel layer by 10 sec oxygen plasma treatment using a FEMTO Plasma Cleaner (8 psi; 100 watts; Diener Electronic, Ebhausen, Germany).

D. Programmable High-Voltage Power Supply Unit

Figure 3:
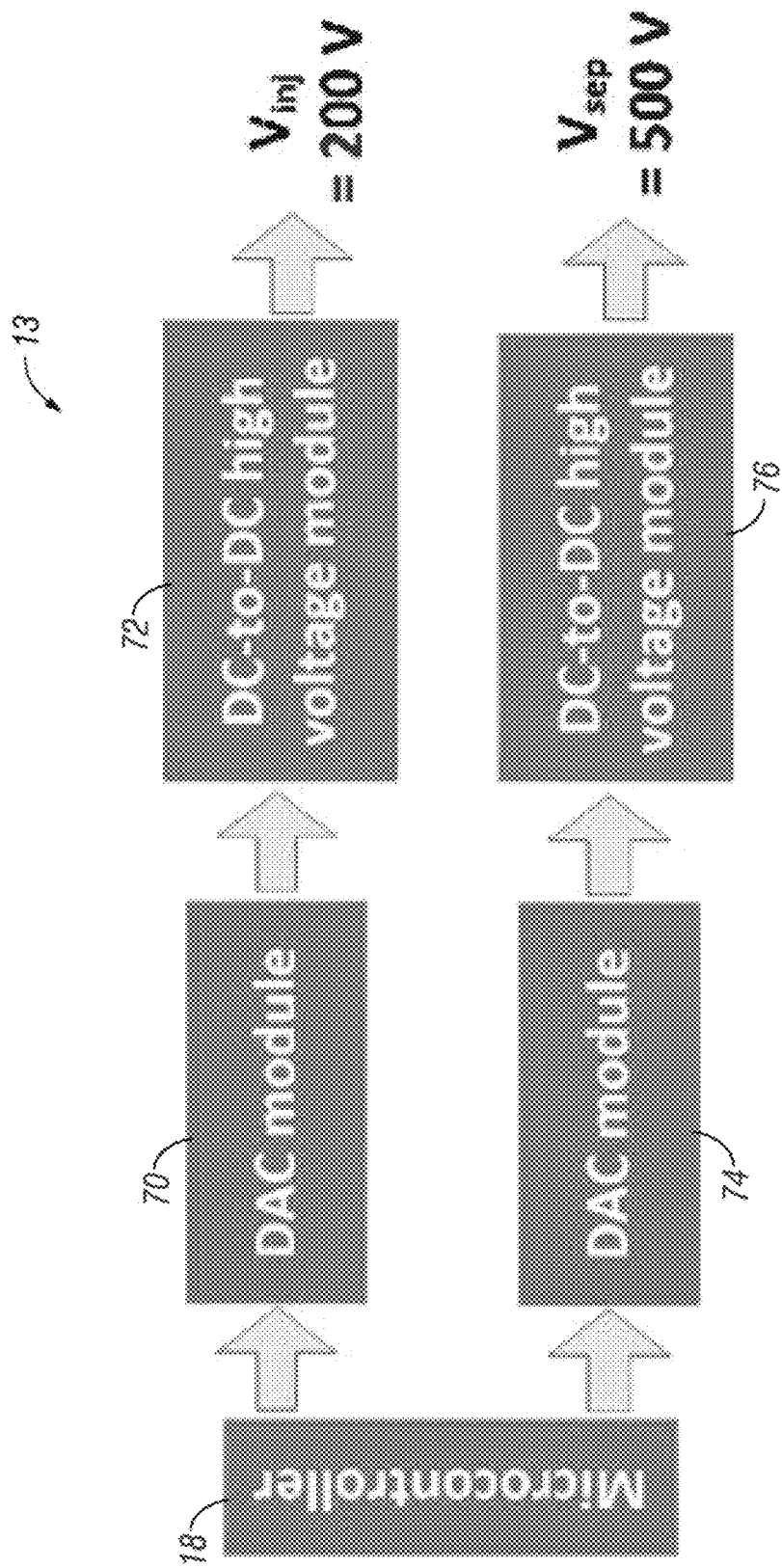
FIG. 3 illustrates an example of a precision high voltage power supply designed to control the voltages for sample injection and ion separation with exemplary embodiments of the invention.

A programmable power supply unit 13 was designed to provide precise electrical potentials to load a sample solution and separate ions. The unit, shown in FIG. 1b and FIG. 3, includes three main parts: Two high voltage DC to DC converters 72 and 76 (CA10P, XP EMCO, Sutter Creek, Calif.), two digital to analog converters 70 (CA10P, XP EMCO, Sutter Creek, Calif.), two digital to analog converters 74 (DACs, MCP4725, Adafruit Industries, New York City, N.Y.), and an Arduino microcontroller 18. The microcontroller controls the two sets of DACs and DC to DC converters, with one set providing a DC voltage Vinj between the sample inlet 26 and the sample waste outlet 28, and the other providing another DC voltage Vsep between the buffer inlet 22 and the buffer waste outlet 24, as shown in FIG. 1(d). Specifically, the microcontroller 18 provides a digital control output, which is converted to an analog DC voltage between 0 and 5 V by the DAC. The DC-to-DC high voltage module elevates the low DC voltage to a high DC voltage up to 1000 V linearly. Therefore, the voltage values Vinj and Vsep can be obtained and flexibly programmed. Two pairs of electric wires are inserted into the corresponding inlets 26, 22 and outlets 28, 24 for applying the two voltages for the sample injection and the ion separation.

E. Conductivity Detection Unit 14

Figure 4:
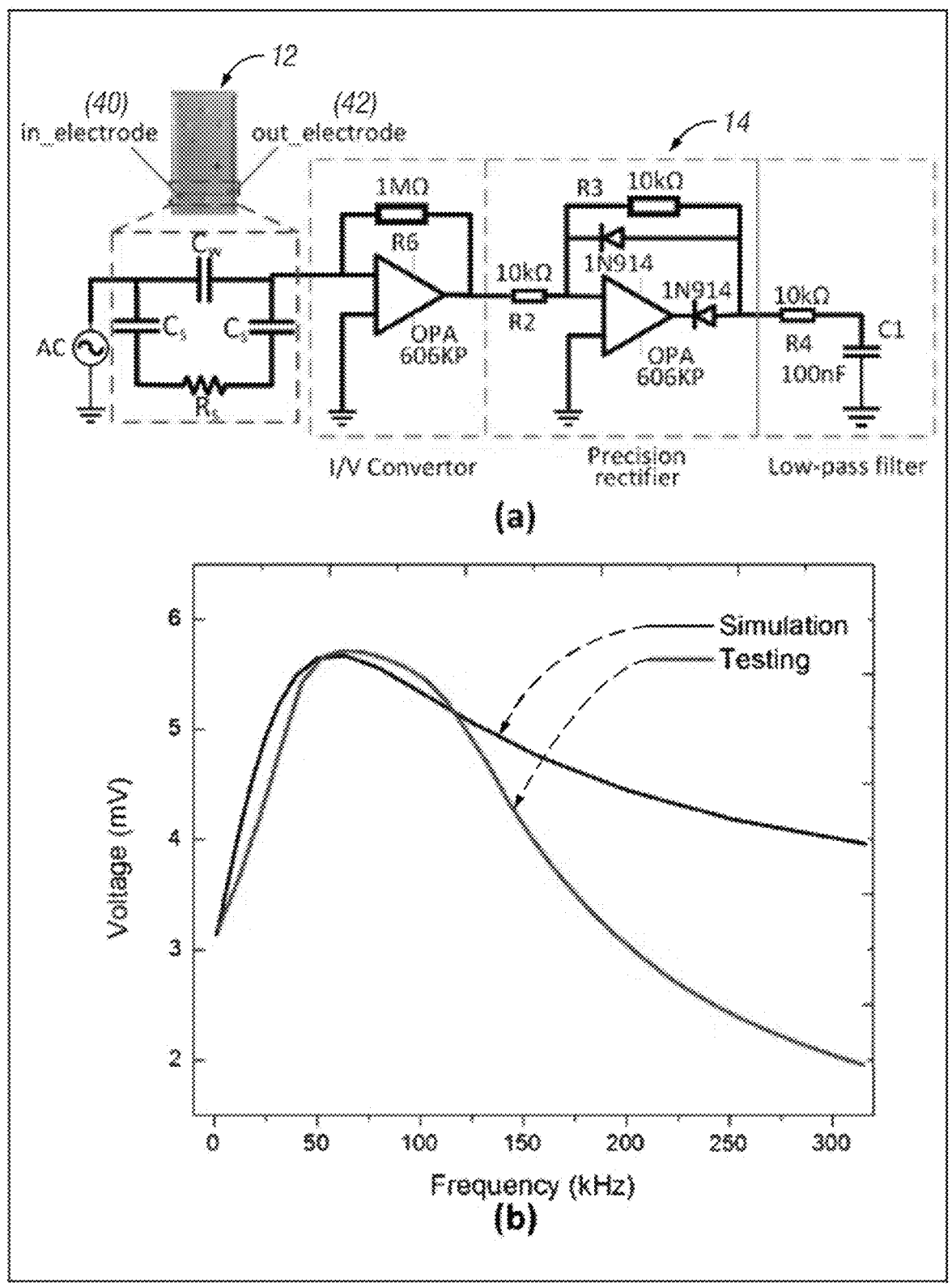
FIG. 4 illustrates exemplary embodiments of the following regarding aspects of the invention: (a) a conductivity detection circuit; (b) a measured versus simulated frequency responses of the microchip.

An electrical circuit model for the two microelectrodes-based detection region of the electrophoretic microchip consists of a bulk solution resistor ($R_S$), two parasitic capacitors ($C_S$) and a bypass capacitor ($C_W$) between the two microelectrodes 40/42, as shown in the red-dashed (left-side) area of the left side of FIG. 4(a). This equivalent circuit was integrated with the conductivity detection unit, as shown in the blue-dashed (right-side) areas in FIG. 4(a). The conductivity detection circuit 14 was designed based on the principle of capacitively coupled conductivity detection [47]. The signal generator provides a sinusoidal signal of 5 $mV_{p-p}$ on one microelectrode of the electrophoretic microchip, while its response is measured at the second microelectrode, through an I-V converter, a rectifier, and a low-pass filter. Thus, besides the sinusoidal activation, the conductivity detection circuit 14 is used to extract, filter, amplify and transfer detected signals for analysis. The I-V convertor transforms the detected current to voltage; the voltage is rectified and low-pass filtered to suppress the "carrier" sinusoid. Two diodes are used to obtain the rectification. The resulting signal from the circuit is acquired by a multimeter. The equivalent circuit of the two electrodes area was analyzed to obtain an equivalent impedance $Z_{eq}$ as in Eq. (4), with its resistive and reactive values given in Eqs. (5) and (6) respectively:

$$Z_{eq}=R_{eq}+jX_{eq} \quad (4)$$

$$R_{eq} = \frac{-R_s X_s X_w + R_s X_w^2}{R_s^2 + (2X_s + X_w)^2} \quad (5)$$

$$X_{eq} = \frac{X_w(4X_s^2 + 2X_s X_w + R_s^2)}{R_s^2 + (2X_s + X_w)^2} \quad (6)$$

$$X_s = -\frac{1}{\omega C_s} \quad (7)$$

$$X_w = -\frac{1}{\omega C_w}. \quad (8)$$

where $R_S$ is the solution resistance, $X_S$ is the parasitic reactance, $X_W$ is the bypass reactance, and ω is the angular frequency of an applied signal.

FIG. 4(b) shows the measured and simulated magnitude frequency response of the output signal of the circuit shown in FIG. 4(a). The component values used in the simulation were identified by measurements: solution resistance, Rs=~140 kΩ, parasitic capacitance, Cs=~20 nF, and bypass capacitance, Cw=~0.8 nF. The maximum response was observed at 62 kHz which was chosen as the carrier sinusoid frequency to favor a high output response for the circuit.

F. Soil Solution Extraction

In additional to the electrophoretic chip 12 and the detection unit 14, a vacuum-based suction unit 80 was also designed for the in situ extraction of soil solution. This unit 80 consists of a suction head 81, a poly(methyl methacrylate) or PMMA-based collection chamber 82, and a mini-vacuum pump 83 (FIG. 5(a)). The suction head 81 structure is as shown in FIG. 5(b). A main component in the suction head 81 is a microfiltration tubular module, consisting of a ceramic capillary tube (hydrophilic membrane composed of a blend of polyvinylpyrrolidine and polyethersulfone; mean pore size: 0.15 μm) and high pressure polyetheretherketone or PEEK tubing. The PEEK tubing of the soil water suction unit 81 is connected with the vacuum input of the PMMA soil water collection chamber 82. The vacuum output is connected the vacuum pump 83 (VMP1625MX-12-90-CH, Virtual Industries, Inc, Colorado Springs, Colo., USA. Mini-Pump with 12 volt MAXON motor; flow rate: 1300 mL/min; develops 18 in/Hg. 16 psi.). This collection chamber 82 has an embedded plastic sphere 86 (FIG. 5(c)). The floating sphere 86 works as a valve and can be set to work in the ON and OFF phases (FIG. 5(d)). When the vacuum pump 83 starts exhausting the air 92 from the PMMA device 82, a low-pressure environment is built in the upper chamber 87/88, and the sphere valve 86 gets stuck to the top end of the vertical channel 85, which is referred to as the "ON" mode. The system then begins to extract solution 91 from soil through the suction head 81 and accumulates it in the chamber atop of the sphere valve (see ref #90 inf FIG. 5(d)). When the extraction is completed, the pump 83 is switched so as to fill air into the chamber (see 92 at right-side state of FIG. 5(d)). This causes the sphere 86 to fall down (to constriction 84), referred to as the "OFF" mode, allowing the collected solution 90 to be delivered below (FIG. 5(d)) for loading into the electrophoretic microchip 12.

The performance of the extraction unit 80 was tested under different soil water potential conditions. When the soil water potential was high, which means wet soil, the extraction rate was also high (e.g., 26.3±1.73 μL/hr at −13 kPa). The extraction rate dropped significantly with decreasing soil water potential (FIG. 5(e)).

Electrophoretic Chip Testing

The buffer solution used for on-chip electrophoresis was chosen to be 2-[N-Morpholino]ethanesulfonic acid (MES)/Histidine (HIS) 30 mM/30 mM, with 4 mmol 18-crown-6 and 0.1% methyl cellulose at 6.0 pH [47]. Both synthetic and extracted soil sample solutions were tested. The synthetic solution included a mixture of $KNO_3$ and $Na_2SO_4$ (each with 50 μM) in deionized (DI) water to evaluate the ability of the sensor to separate different ions, and different concentration solutions of $KNO_3$ in DI water to test the ability of the sensor to quantify nitrate ion concentrations.

Two types of real samples were prepared. The real sample of the first type (Type 1) was extracted from the soil samples collected at different locations of a Z. mays (type of maize) farm field at the Agricultural Engineering and Agronomy Research Farm (Boone, Iowa). Briefly, 10 g of field moist soil was weighed in a specimen cup. 50 mL of DI water was then added to the specimen cup and shaken on a reciprocal shaker for 1 hr. After shaking, the solution was filtered using Whatman #1 filter paper and the filtrates were collected, diluted with DI water at ratio 1 to 10, and stored at 4° C. until taken out for injection into the electrophoretic microchip [48].

The real sample solution of the second type (Type 2) was collected directly from soils by the presented soil solution extraction unit. The suction head was insert into the soil, with the extraction unit running for 1 hour to extract about 20 μL of soil solution under the soil water potential of −13 kPa.

To perform the ion concentration measurement on the electrophoretic microchip, the MES/HIS buffer solution was loaded into both the microfluidic channels by using a 3 mL syringe (Becton Dickinson, N.J., USA) with a microbore tubing (Cole-Parmer, Ill., USA). Subsequently, a specific sample solution was placed at the inlet of the microchip using a pipette (Thermo Scientific, MA, USA). Next, the sample solution was injected into the shorter channel by generating and applying a 200 V between the sample inlet and the sample waste outlet for 6 sec to allow filling the intersection. Subsequently, ion separation was carried out by applying 500 V between the buffer reservoir and the buffer waste reservoir for 450 sec. The conductivity detection at the electrode was performed using a 5 $mV_{p-p}$ excitation voltage at 62 kHz. After each test-run, the microchip was rinsed with 1 mL buffer solution for 10 times.

Results and Discussion

A. Separation of Ions

FIG. 6 shows the output voltage of the microchip system over a period of 450 sec when the device was used to separate the anions of $NO_3$ and $SO_4$ (50 μM each) present in the synthetic sample solution. The experimental result clearly shows two voltage peaks at two different times owing to different ionic mobilities of the $NO_3$ and $SO_4$ ions. Note while the concentrations of the two ions were the same in the synthetic sample solution, their peak intensities were different, owing to the differences in their changes and ionic conductivities.

B. Sensitivity and Detection-Limit from Single Ion Detection

For the sensitivity and the detection-limit analysis, nitrate sensing was performed using the synthetic nitrate solutions of concentrations 20, 40, 60, 80, and 100 mM. Each solution was loaded into the same microchip for 3 different detection runs. FIG. 7(a) shows the peaks corresponding to 20, 40, 60, 80, and 100 μM of nitrate ion concentrations, all of which appeared around the same time (187±3 s), indicating the high temporal accuracy of the sensor for a given ion species. Furthermore, the five nitrate concentrations can be clearly distinguished by their corresponding peak levels. FIG. 7(b) demonstrates that the voltage output of the sensor is almost linear to the input nitrate concentration. A linear fit of the data (FIG. 7(b)) indicates that the sensitivity of the sensor for the detection of the nitrate ions is approximately 0.0915 mV/μM.

The limit of detection (LOD) of the presented sensor is defined to be three times the standard deviation over the average of the voltage readout, in the absence of any analyte. The noise floor of the sensor is 0.30±0.12 mV. Therefore, according to the above-mentioned definition, the LOD of the sensor is equivalent to a nitrate concentration that will result in an output voltage of 0.3+(3×0.12) mV=0.66 mV. This corresponds to LOD of around 7.25 μM. As shown in the inset of FIG. 7(a), it is also confirmed that the minimum detectable nitrate concentration of this sensor is 7.25 which is an improvement compared to some previously reported values [50], and much higher than the amount found in agricultural soil. While this LOD is slightly higher than some ISE-based and enzymatic electrochemical sensors [26], the electrophoretic sensor has the advantage of being label-free, thereby eliminating the limit on sensor life due to the limited life of the ion selective materials.

C. Soil Solution Testing

The developed sensor was used to detect the major anions in the two types of real sample solutions collected from the soils. As mentioned in Section III, the first-type soil sample solution was obtained through the standard shaking and filtering process, and the second-type soil sample solution was collected directly by the developed extraction unit. FIG. 8 shows the result corresponding to the separated anions, under the applied electrical field, detected as time-separated voltage peaks, and served as a proof-of-principle.

In order to identify the ion types corresponding to the observed peaks, we tested four types of standard solutions independently using the microchip, each solution included only a single type of anion: chloride ($Cl^-$), nitrate ($NO_3^-$), sulphate ($SO_4^{2-}$), and dihydrogen phosphate ($H_2PO_4^-$), respectively (FIG. 8 (a)). These included the three important nutrients (nitrogen, phosphorus, and sulphur), plus chlorine that is considered to be the main interfering species for nitrogen. Although there are more than 4 peaks, especially in the solution extracted using a standard method, at this point only the four ions were cared to identify, for demonstrating a proof-of-principle. As discussed below, the 0.15 μm mean pore size of the extraction unit's suction head is able to filter out many extraneous particles/microbes.

The measured peaks for the 4 known ions were mapped against the results of the soil sample solution tests (FIG. 8(b)(c)). The difference between plots in FIG. 8(b) versus in FIG. 8(c) revealed a curious fact that the different extraction methods can yield different number of ion species. In fact, the ones present in the solution obtained through a standard extraction method (in FIG. 8(b)) may not be the same as the ones available to the plants. On the other hand, since the soil solution extraction unit works on the principle of the water potential difference, and which is how the plants are also able to ingest nutrients, the solution extracted using the extraction unit provides a more realistic picture of what soil ions may be available to the plants. Furthermore, since the pore size (0.15 μm) of the suction head used in the extraction unit is much smaller than the pore size of Whatman #1 filter paper (11 μm) used in the standard solution extraction method, more extraneous particles/microbes were filtered out by the extraction unit, which also explains the fewer number of detected peaks in the solution extracted by the suction unit.

Using the result of mapping of the plots corresponding to the 4 known ion types against those of the two extracted solutions (FIG. 8(b)(c)), the peaks were labeled in FIG. 8 accordingly.

It is clear from the figure that the four ions in questions could be separated from each other, including nitrogen from chlorine. Furthermore, using the calibration plot in FIG. 7(b), the detected nitrate concentration in the soil sample was found to be 210.3±3.52 which is within a 9% error-margin of the concentration value 191.2±2.39 μM obtained using a sophisticated benchtop ultraviolet spectrophotometer. The slightly higher measured value for nitrate can be understood as follows: due to the closeness of the mobilities of chloride and nitrate (as noted from the proximity of their peaks), some residual chloride ions passed through the detection area while the nitrate ions started to go through that area, resulting in a slightly enhanced signal. In order to correct for such enhancement due to the overlap of the ions, one possible method would be to mathematically characterize the overlap, and algorithmically correct the reported value of the nitrate concentration. Another approach would be to increase the length of the separation channel to allow a larger gap between the two peaks and their better separation. Both these approaches are directions for future research.

CONCLUSION

A microfluidic microchip nutrient sensing system was developed to extract, separate, detect, and quantify nutrient ions in soil sample solutions. The system can be used for extracting and testing analytes from other sources (e.g., water). Using this system, a mixture of anions present in the soil solution extracted using the new suction unit as well as from an existing standard method was separated and detected via distinguishing peaks, separated over time. Further, a good linear relation between a single ion (nitrate) concentration and detected signal peak was demonstrated. This together with a limit of detection of ~7.25 μM for nitrate ions demonstrated a good performance of the proposed detection system. The design and implementation of the soil solution extraction unit makes the entire sensing system suited for in situ applications. The extraction unit is driven by the water potential gradient, matching how the plants ingest nutrients, unlike the standard soil solution extraction methods. Also, the smaller-sized pores in the suction heads ensures that many of the impurities (particles/microbes) are automatically filtered out. In order to make the sensing system fully ready for an in situ adoption, it would additionally require its integration with a wireless communication unit, such as one reported in [4]. A fully integrated sensing system has great prospects in nutrient management for precision farming.

As will be appreciated by those skilled in the art, the principles of these embodiments can be applied to: (i) integrating the electrophoretic microchip sensor system with the soil solution extraction unit, a pumping unit for delivery of buffer solution and waste, external storage and waste reservoirs, and a wireless communication capability to realize a finished prototype for in situ soil nutrient monitoring, (ii) thinning down the glass substrate to further increase the output signal strength and thereby the sensitivity and LOD, (iii) optimizing the detection circuit to reduce noise floor and thus further lowering the detection limit of the system, and (iv) expanding the ability of the device to detect and quantify also the cations besides the anions.

REFERENCES [EACH OF WHICH IS INCORPORATED BY REFERENCE HEREIN IN ITS ENTIRETY]

[1] A. Bah, S. Balasundram, and M. Husni, "Sensor technologies for precision soil nutrient management and monitoring," *Am. J. Agri. & Biol. Sci.*, vol. 7, no. 1, pp. 43-49, January 2012
[2] K. Goulding, S. Jarvis, and A. Whitmore, "Optimizing nutrient management for farm systems," *Philos. Trans. R. Soc. Lond., B, Biol. Sci.*, vol. 363, no. 1491, pp. 667-80, February 2008.
[3] H. Sahota, R. Kumar, and A. Kamal, "A wireless sensor network for precision agriculture and its performance," *WIREL COWUN MOB COM*, vol. 11, no. 12, pp. 1628-1645, December 2011.
[4] J. Huang, R. Kumar, A. Kamal, and R. Weber, "Development A Wireless Soil Sensor Network", 2008 American Society of Agriculture and Biosystems Engineering, Providence, R.I., June 2008.
[5] P. Robert, "Precision agriculture: a challenge for crop nutrition management," *Plant Soil*, vol. 247, no. 1, pp. 143-149, November 2002.
[6] N. Zhang, M. Wang, and N. Wang, "Precision agriculture—a worldwide overview," *Comput. Electron. Agric.*, vol. 36, no. 2, pp. 113-132, November 2002.
[7] C.-H. Ho, S.-H. Lin, H.-C. Hu et al., "CHL1 functions as a nitrate sensor in plants," *Cell*, vol. 138, no. 6, pp. 1184-1194, September 2009.
[8] G. Pandey, R. Kumar, and R. J. Weber, "A Low RF-Band Impedance Spectroscopy Based Sensor for In Situ, Wireless Soil Sensing," *IEEE Sens. J.*, vol. 14, no. 6, pp. 1997-2005, February 2014.
[9] F. Kizito, C. Campbell, G. Campbell et al., "Frequency, electrical conductivity and temperature analysis of a low-cost capacitance soil moisture sensor," *J. Hydrol.*, vol. 352, no. 3, pp. 367-378, May. 2008.
[10] S. Staggenborg, M. Carignano, and L. Haag, "Predicting soil pH and buffer pH in situ with a real-time sensor," *Agron. J.*, vol. 99, no. 3, pp. 854-861, May. 2007.
[11] T. Jackson, K. Mansfield, M. Saafi et al., "Measuring soil temperature and moisture using wireless MEMS sensors," *Measurement*, vol. 41, no. 4, pp. 381-390, May. 2008.
[12] Z. Zou, A. Jang, E. MacKnight et al., "Environmentally friendly disposable sensors with microfabricated on-chip planar bismuth electrode for in situ heavy metal ions measurement," *Sens. Actuators, B Chem.*, vol. 134, no. 1, pp. 18-24, August 2008.
[13] J. V. Sinfield, D. Fagerman, and O. Colic, "Evaluation of sensing technologies for on-the-go detection of macronutrients in cultivated soils," Comput. *Electron. Agric.*, vol. 70, no. 1, pp. 1-18, January 2010.
[14] D. Corwin, and S. Lesch, "Apparent soil electrical conductivity measurements in agriculture," *Comput. Electron. Agric.*, vol. 46, no. 1, pp. 11-43, March 2005.
[15] K. Sudduth, S. Drummond, and N. Kitchen, "Accuracy issues in electromagnetic induction sensing of soil electrical conductivity for precision agriculture," *Comput. Electron. Agric.*, vol. 31, no. 3, pp. 239-264, May. 2001.
[16] E. Ben-Dor, and A. Banin, "Near-infrared analysis as a rapid method to simultaneously evaluate several soil properties," *Soil Sci. Soc. Am. J.*, vol. 59, no. 2, pp. 364-372, March 1995.
[17] J. Reeves, G. McCarty, and T. Mimmo, "The potential of diffuse reflectance spectroscopy for the determination of carbon inventories in soils," *Environ. Pollut.*, vol. 116, pp. S277-S284, March 2002.
[18] R. Verschoore, J. Pieters, T. Seps et al., "Development of a sensor for continuous soil resistance measurement," *Precision Agriculture*. Wageningen Academic Publishers, Wageningen, The Netherlands, 2003. pp. 689-695.
[19] T. E. Grift, M. Z. Tekeste, and R. L. Raper, "Acoustic compaction layer detection," *Trans. ASAE*, vol. 48, no. 5, pp. 1723-1730, 2005.
[20] S. Birrell, and J. Hummel, "Multi-sensor ISFET system for soil analysis," *Precision Agri.*, vol. 97, pp. 459-468, 1997.
[21] D. L. Jones, "Organic acids in the rhizosphere—a critical review," *Plant Soil*, vol. 205, no. 1, pp. 25-44, August 1998.
[22] C.-W. Chang, D. A. Laird, M. J. Mausbach et al., "Near-infrared reflectance spectroscopy-principal components regression analyses of soil properties," *Soil Sci Am J.*, vol. 65, no. 2, pp. 480-490, March 2001.
[23] R. R. Price, J. W. Hummel, S. J. Birrell et al., "Rapid nitrate analysis of soil cores using ISFETs," *Trans. ASAE*, vol. 46, no. 3, pp. 601, 2003.
[24] E. Bakker, and M. Telting-Diaz, "Electrochemical sensors," *Anal. Chem.*, vol. 74, no. 12, pp. 2781-2800, June 2002.
[25] M. A. Ali, W. Hong, S. Oren et al., "Tunable bioelectrodes with wrinkled-ridged graphene oxide surfaces for electrochemical nitrate sensors," *RSC Adv.* July 2016.
[26] A. T. Woolley, D. Hadley, P. Landre et al., "Functional integration of PCR amplification and capillary electrophoresis in a microfabricated DNA analysis device," *Anal. Chem.*, vol. 68, no. 23, pp. 4081-4086, December 1996.
[27] M. W. Lada, T. W. Vickroy, and R. T. Kennedy, "High temporal resolution monitoring of glutamate and aspartate in vivo using microdialysis on-line with capillary electrophoresis with laser-induced fluorescence detection," *Anal. Chem.*, vol. 69, no. 22, pp. 4560-4565, November 1997.
[28] C. S. Effenhauser, G. J. Bruin, A. Paulus et al., "Integrated capillary electrophoresis on flexible silicone microdevices: analysis of DNA restriction fragments and detection of single DNA molecules on microchips," *Anal. Chem.*, vol. 69, no. 17, pp. 3451-3457, September 1997.
[29] C. L. Colyer, T. Tang, N. Chiem et al., "Clinical potential of microchip capillary electrophoresis systems," *Electrophoresis*, vol. 18, no. 10, pp. 1733-1741, April 1997.
[30] Y. Huang, K. L. Ewalt, M. Tirado et al., "Electric manipulation of bioparticles and macromolecules on microfabricated electrodes," *Anal. Chem.*, vol. 73, no. 7, pp. 1549-1559, February 2001.
[31] Z. Liang, N. Chiem, G. Ocvirk et al., "Microfabrication of a planar absorbance and fluorescence cell for integrated capillary electrophoresis devices," *Anal. Chem.*, vol. 68, no. 6, pp. 1040-1046, March 1996.
[32] M. Albin, R. Weinberger, E. Sapp et al., "Fluorescence detection in capillary electrophoresis: evaluation of derivatizing reagents and techniques," *Anal. Chem.*, vol. 63, no. 5, pp. 417-422, March 1991.

[33] J. Webster, M. Burns, D. Burke et al., "Monolithic capillary electrophoresis device with integrated fluorescence detector," *Anal. Chem.*, vol. 73, no. 7, pp. 1622-1626, February 2001.

[34] M. L. Chabinyc, D. T. Chiu, J. C. McDonald et al., "An integrated fluorescence detection system in poly (dimethylsiloxane) for microfluidic applications," *Anal. Chem.*, vol. 73, no. 18, pp. 4491-4498, August 2001.

[35] C. Dongre, H. J. Hoekstra, and M. Pollnau, "Capillary electrophoresis and multicolor fluorescent DNA analysis in an optofluidic chip," in *Capillary Electrophoresis and Microchip Capillary Electrophoresis: Principles, Applications, and Limitations*, Hoboken, N.J.: John Wiley & Sons, Inc., 2013. pp. 247-266.

[36] H. Craighead, "Future lab-on-a-chip technologies for interrogating individual molecules," *Nature*, vol. 442, no. 7101, pp. 387-393, July 2006.

[37] D. R. Reyes, D. Iossifidis, P.-A. Auroux et al., "Micro total analysis systems. 1. Introduction, theory, and technology," *Anal. Chem.*, vol. 74, no. 12, pp. 2623-2636, May. 2002.

[38] P.-A. Auroux, D. Iossifidis, D. R. Reyes et al., "Micro total analysis systems. 2. Analytical standard operations and applications," *Anal. Chem.*, vol. 74, no. 12, pp. 2637-2652, May. 2002.

[39] A. T. Woolley, and R. A. Mathies, "Ultra-high-speed DNA fragment separations using microfabricated capillary array electrophoresis chips," *Proc. Natl. Acad. Sci.*, vol. 91, no. 24, pp. 11348-11352, November 1994.

[40] M. Smolka, D. Puchberger-Enengl, M. Bipoun, et al. "A mobile lab-on-a-chip device for on-site soil nutrient analysis." *Precision Agriculture*, pp: 1-17, May. 2016.

[41] T. Kappes, B. Galliker, M. A. Schwarz et al., "Portable capillary electrophoresis instrument with amperometric, potentiometric and conductometric detection," *Trends Anal. Chem.*, vol. 20, no. 3, pp. 133-139, March 2001.

[42] E. Knutson, and K. Whitby, "Aerosol classification by electric mobility: apparatus, theory, and applications," *J. Aerosol Sci.*, vol. 6, no. 6, pp. 443-451, November 1975.

[43] G. Yao, "A Computational Model for Simulation of Electroosmotic Flow in Microsystems." *Technical proceedings of the 2003 nanotechnology conference and trade show*, vol. 1, no. 9, 2003, pp. 218-221.

[44] V. M. Ugaz, and J. L. Christensen, "Electrophoresis in microfluidic systems," in *Microfluidic Technologies for Miniaturized Analysis Systems*, New York: Springer, 2007. pp. 393-438.

[45] M. R. Wright, "Conductance: The Ideal Case" in *An introduction to aqueous electrolyte solutions*, Hoboken, N.J.: John Wiley & Sons, Inc., 2007. pp. 421-474

[46] F. Opekar, P. Tůma, and K. Štulik. "Contactless impedance sensors and their application to flow measurements," *Sensors*, 13, no. 3, 2013, pp. 2786-2801.

[47] J. A. Fracassi da Silva, and C. L. do Lago, "An oscillometric detector for capillary electrophoresis," *Anal. Chem.*, vol. 70, no. 20, pp. 4339-4343, September 1998.

[48] P. Schmitt-Kopplin, "Determination of Small Ions With Capillary Electrophoresis and Contactless Conductivity Detection" in *Capillary electrophoresis: methods and protocols,* Totowa, N.J.: Humana Press, 2008. pp. 3-19.

[49] R. Hood-Nowotny, N. Hinko-Naj era Umana, E. Inselbacher, P. Oswald-Lachouani, and W. Wanek, "Alternative methods for measuring inorganic, organic, and total dissolved nitrogen in soil," *Soil Sci. Soc. Am. J.* 74: 1018-1027, May 2010.

[50] P. Kubáň, and P. C. Hauser, "Application of an external contactless conductivity detector for the analysis of beverages by microchip capillary electrophoresis," *Electrophoresis*, vol. 26, no. 16, pp. 3169-3178, July 2005.

D. Options and Alternatives

As mentioned, the invention can take many forms and embodiments and is not limited to those described above. Variations obvious to those skilled in the art will be included with the invention.

Some additional examples of options and alternatives follow.

Applications

Measurement of soil nutrients can be used in a number of ways. For example, they can be used to vary the rate of nitrogen application to a field that has been measured for nitrate.

The invention can use nitrate measurements for other purposes. And, as will be appreciated by those skilled in the art, the invention can be used to detect other ionic concentrations in liquid samples. For example, the invention has applicability to any concentrated liquid. This implicates use in applications such as toxicity in food washes, toxicity in water, and characteristics of bodily fluids, to name a few.

The collected sample solution could be geo-indexed to field position by some trigger that would reference GPS (or other geospatial system) to that sampling location. See, e.g., GPS-enabled precision agriculture system, such as are well-known. Typically there would be some pre-processing to collect the sample from soil for injection into the electrophoretic chip.

One example of sample collection that we would include is:

1. Microfluiding technology for suction from soil and pumping into the electrophoretic chip.

The basic rules regarding automatic collection of soil samples from an agricultural field include:

a. minute quantity of the order of 10 microliter, sufficient for electrophoretic measurement, but not to perturb the soil concentration.

b. From desired locations in field.

c. From desired depth in the field.

d. Separation of relevant soil solution sample by filtering out debris and any gases.

U.S. Pat. No. 5,355,815 to inventor Monson entitled Closed-Loop Variable Rate Applicator and U.S. Pat. No. 7,216,555 to inventors Drummond et al. entitled System and Method for Mobile Soil Sampling (both incorporated by reference herein) are a few examples of a variable rate fertilizer application and gives details about how a fertilizer applicator rate can be controlled.

Soil Solution Collection

The technique for soil solution collection can involve the step of gathering soil samples and preprocessing the sample into a usable, minute quantities for injection into the electrophoretic chip, and can take various forms or embodiments.

The primary way of soil solution collection with the invention is to place the sensors in the soil and take measurements in situ. This can include just a single sensor or a plurality distributed around a field. As indicated in FIG. 12, one way to obtain soil solution sample in situ is by burying a porous ceramic capillary member in the soil. A vacuum is created which sucks the soil solution into a microfluidic circuit. As shown in FIG. 12, the sample is then flown along a buffer solution for electrophoretic separation of ions present in the sample solutions. It is to be noted that relatively minute quantities of soil sample are sufficient to obtain results. Circuitry controls the processes, including when samples are collected and flown. As explained above, electrophoretic processes on the sensor result in current signals that are digitized and logged. That data can be processed into indications of presence and concentrations of ionic substances of interest. As will be appreciated, the geospatial location of in situ sensors can be obtained and stored, and tagged to each sensor's measurements.

Having in situ sensors includes at least these types of benefits:
1. Does not perturb the field operations;
2. Does not affect the growth of plants;
3. Allows on-site measurements;
4. Allows fast measurements (within 10 minutes);
5. Allows immediate response of variable-rate application.

Some alternatives for in situ application are as follows:
1. The detection unit can be embedded or above ground. Depth of sampling can be one depth, or different depths (by using vertically positioned porous ceramics at the same field location). One example is to place at least one sampler at the plant root level.
2. The sensor can be automated as to sampling time, frequency, etc. A typical frequency could be same as the number of fertilizer applications within a growing season, but this can be varying according to desire or need. For example, it dependent on type of plant, what the farmer desires, or the number of times fertilizer is applied, to name but a few factors.

An alternative could be obtaining samples on the move and transferring them to the microfluidic electrophoretic network. U.S. Pat. No. 7,216,555 to inventors Drummond et al. entitled System and Method for Mobile Soil Sampling, and U.S. Pat. No. 7,575,069 to inventor Pavlik entitled Mobile Soil Sampling Device With Vacuum Collector (both incorporated by reference herein) discuss background details of such systems.

A possible specific example is as follows.

It is to be understood, including by reference to U.S. Pat. No. 7,216,555 to inventors Drummond et al., that such a sampling would typically receive soil as the implement moves across the ground 100. The location of the sample can be correlated to a geospatial location by a precision ag system 102, which typically use GPS and/or inertial navigation systems. See, e.g., FIGS. 9-11 at ref. #14. An implement 106 pulled by tractor 104 can collect soil samples, bring them to chip 14 and inform precision ag unit 102 of nutrient concentration. Precision ag unit 102 could instruct a metered applicator 107 of 106 to apply the nutrient (e.g. $N_2$) from a nutrient supply 108 modulated by the nutrient concentration on-the-go measurement of chip 14.

Relatively minute soil samples are retrieved as the implement moves across the ground. There could be some type of tool 80 inserted into the soil with an opening to receive soil, and processed further to extract solution.

For comparison, an example of a commercially available system that can be transported on a pickup truck to a field, gather soil samples manually and then use the portable instrument to estimate such things as nitrate levels in the soil is 360 SOILSCAN™ from https://360yieldcenter.com/product-support (incorporated by reference herein). It shows ways in which the instrument can communicate wirelessly to tablet computers, store soil test data digitally, and link that information to precision ag system geospatial maps and the like.

Injection of Sample

Lin, Che-Hsin, Double-L Injection Technique For High-Performance Capillary Electrophoresis Detection in Microfluidic Chips, J. Micromech. Microeng. 14 (2004) 639-646 (incorporated by reference herein) describes a double L configuration for injection of a sample and a buffer solution. Alternatives are possible.

Wang, Qinggang, Mobility-Based Selective On-Line Preconcentration of Proteins In Capillary Electrophoresis By Controlling Electroosmotic Flow; J. Chromatography A, 1025 (2004) 139-146 (incorporated by reference herein) describes background principles of electrophoretic separation involving control of electroosmotic flow.

Conductivity Detection

Tanyanyiwa, Jatisai, et al, Capacitively Coupled Contactless Conductivity Detection for Microchip Capillary Electrophoresis, Anal. Chem. 2002, 74, 6378-6382 and Zeman, Andreas, Capacitively Coupled Contactless Conductivity Detection in Capillary Electrophoresis, Electrophoresis 2003, 24, 2125-2137 (both incorporated by reference herein) give examples of how conductivity sensing or detection via electrodes relative a substance of interest can be performed and calibrated.

The invention claimed is:

1. A method for detection of chemical constituents in an analyte comprising:
   a. collecting an analyte sample;
   b. loading a buffer solution in an electrophoretic channel, wherein the electrophoretic channel comprises a microfluidic separation channel;
   c. loading the analyte sample into the buffer solution, wherein the loading of the analyte sample comprises:
      i. running of the buffer solution through the microfluidic separation channel;
      ii. injecting the analyte sample into the running buffer solution;
      iii. directing the running buffer solution and injected analyte sample into the microfluidic separation channel by:
         a. a double L injection configuration;
         b. microfluidic pneumatic valving; and
         c. controlled timing for injecting the buffer solution and analyte sample;
   d. flowing the analyte sample through the electrophoretic channel containing the buffer solution;
   e. separating one or more ionic species in the analyte sample/buffer solution by electrophoresis;
   f. measuring conductivity of the one or more separated ionic species; and
   g. comparing measured and detected (i) time of arrival and (ii) conductivity magnitude of the electrophoretically-separated one or more ionic species to reference time of arrival and conductivity values of known ionic species to estimate presence and concentration of the one or more ionic species in the sample.

2. The method of claim 1 wherein the electrophoresis is controlled by control of an electric field along the electrophoretic channel.

3. The method of claim 1 wherein the conductivity is measured with a set of electrodes at an electrophoretic separation zone along the electrophoretic channel.

4. The method of claim 1 wherein:
   a. the analyte sample is label-free; and
   b. the ionic species comprises inorganic ions.

5. The method of claim 1 applied to an analyte sample related to one of:
a. soil nutrients;
b. soil constituents;
c. water quality;
d. food safety; and
e. bodily fluids.

6. The method of claim 1 applied to an analyte sample from an agricultural field wherein the sample is tested for ionic species and their concentrations associated with soil nutrients.

7. The method of claim 6 wherein the soil nuts cents comprise one or more of:
a. nitrate;
b. chloride;
c. perchlorate;
d. sulphate;
e. dihydrogen phosphate;
f. hydrogen phosphate;
g. potassium;
h. calcium;
i. sodium; and
j. other ions.

8. The method of claim 7 further comprising:
a. utilizing soil nutrient measurements from analyte samples from a plurality of in situ detectors placed at different positions in an agricultural field;
b. tagging each soil nutrient measurement to a geo-spatial position related to the agricultural field; and
c. utilizing the mapped soil nutrient measurements to inform a nutrient applicator as to amount of nutrient to apply at or around each measurement position.

9. An ion-based, soil nutrient sensor comprising:
a. a sampling head insertable into soil, the sampling head comprising a porous capillary member exposed to the soil, the porous capillary member having a pore size effective to pass soil solution from soil into the porous capillary member but block debris;
b. a chip body;
c. an electrophoresis microfluidic channel network on the chip body including;
i. an input section for loading an analyte sample and a buffer solution;
ii. an elongated separation channel between the input section and an outlet section;
d. an electrical circuit to set up a controllable electrical field along the separation channel sufficient to separate one or more ionic species in the sample solution over time;
e. a detection circuit at an end of the separation channel at a separation zone to measure conductivity due to the separated ions and generate an output signal comprising conductivity measurements for use to correlate to ionic species and concentrations of interest;
f. a soil solution sample collection chamber in fluid communication with the sampling head and the input section of the microfluid channel network;
g. an air-pressure-controlled valve between the sampling head and the soil sample collection chamber;
h. a reversible air pump in fluid communication with the sampling head and the air-pressure-controlled valve, the reversible air pump providing negative air pressure vacuum suction to the sampling head and air-pressure-controlled valve to influence a soil solution sample into the head from the soil but block communication of the sample to the soil sample collection chamber during a sample acquisition, and providing positive air pressure to open the air-pressure-controlled valve to release at least a portion of the acquired soil solution sample to the soil sample collection chamber in preparation for injection into the microfluidic channel network for electrophoretic separation; and
i. a programmable controller in electrical communication with:
(1) the reversible air pump to automatically control the sample acquisition and release,
(2) the electrical circuit to control the controllable electrical field along the separation channel, and
(3) the detection circuit to facilitate the conductivity measurements.

10. The sensor of claim 9 wherein the electrophoresis channel network is formed in the chip body by soft lithography techniques and covered with a glass substrate on which are positioned a set of measuring electrodes associated with the detection circuit.

11. The sensor of claim 9 wherein the input section comprises pneumatic microfluidic valves to control the loading of the analyte sample and buffer solutions, and to deter leakage.

12. The sensor of claim 9 wherein the input section comprises a microfluidic double L injection configuration.

13. The sensor of claim 9 wherein the chip body encapsulates the microfluidic circuit and is operatively connected to the sample collection head.

14. The sensor of claim 9 wherein the detector circuit output signal is operatively communicated to a controller/processor that correlates the conductivity measurements to one or more ionic species and concentrations of interest.

15. The sensor of claim 9 wherein:
a. the sensor is installed in situ in an agricultural field;
b. the acquired sample is the soil solution in the agricultural field;
c. the ionic species of interest are soil nutrients; and
d. the detector circuit output signal is adapted for operative communication to a precision agricultural system which can merge geospatial information related to the field with each sample measurement location for matching soil nutrient concentrations to locations in an agricultural field.

16. The sensor of claim 9 wherein the conductivity detector circuit comprises a set of gold electrodes outside of and on one side of the separation channel.

17. The sensor of claim 9 connected to a read out which informs a user of presence of and concentration of one or more ionic species of interest.

18. The sensor of claim 9 in operative communication with a digital computing device or controller.

19. A system comprising:
a. a sensor according to claim 9;
b. a control unit for providing a first, relatively high, controlled electrical field for the input section injection of the acquired sample into the buffer, and a second, relatively high, controlled electrical field for separation of ionic species along the electrophoretic channel;
c. a control unit for providing a relatively low excitation voltage to one of a set of electrodes of the detection circuit at a detection zone of the electrophoretic channel;
d. an electrical connection between the electrodes and a processor which:
i. compares conductivity measurements at the electrodes to reference calibrations regarding presence and concentration of ionic species of interest; and ii. produces ionic species detection and concentration signals related to the comparison.

20. The system of claim 19 further comprising a precision agricultural system with geospatial sensors and a nutrient application implement wherein:
   a. the acquired sample comprises the soil solution from an agricultural field;
   b. the ionic species of interest comprises one or more soil nutrients;
   c. the ionic species detection and concentration signals from the sensor are used to modulate application rate of a nutrient relative to geospatial information correlated to the agricultural field.

* * * * *

UNITED STATES PATENT AND TRADEMARK OFFICE
CERTIFICATE OF CORRECTION

PATENT NO. : 10,564,122 B1
APPLICATION NO. : 15/789033
DATED : February 18, 2020
INVENTOR(S) : Zhen Xu, Liang Dong and Ratnesh Kumar Page 1 of 1

It is certified that error appears in the above-identified patent and that said Letters Patent is hereby corrected as shown below:

Column 21, Claim 7, Line 12:
DELETE: "nuts cents"
INSERT: --nutrients--

Signed and Sealed this
Nineteenth Day of May, 2020

Andrei Iancu
*Director of the United States Patent and Trademark Office*